US011173309B2

(12) United States Patent
Torgerson

(10) Patent No.: US 11,173,309 B2
(45) Date of Patent: Nov. 16, 2021

(54) USER INTERFACE FOR IDENTIFYING MIDLINES OF SPINAL CORD

(71) Applicant: Medtronic, Inc., Minneapolis, MN (US)

(72) Inventor: Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 133 days.

(21) Appl. No.: 16/545,830

(22) Filed: Aug. 20, 2019

(65) Prior Publication Data
US 2019/0366096 A1   Dec. 5, 2019

Related U.S. Application Data
(63) Continuation of application No. 15/639,126, filed on Jun. 30, 2017, now Pat. No. 10,398,899.

(51) Int. Cl.
*A61N 1/36* (2006.01)
*A61N 1/05* (2006.01)
(Continued)

(52) U.S. Cl.
CPC ....... *A61N 1/36132* (2013.01); *A61N 1/0551* (2013.01); *A61N 1/0553* (2013.01);
(Continued)

(58) Field of Classification Search
CPC .............. A61N 1/36132; A61N 1/0551; A61N 1/36139; A61N 1/0553; A61N 1/37241; A61N 1/36071; G16H 20/30
See application file for complete search history.

(56) References Cited

U.S. PATENT DOCUMENTS 8,463,400 B2   6/2013   Hegi et al.
8,560,080 B2   10/2013  Goetz et al.
(Continued)

FOREIGN PATENT DOCUMENTS

| CA | 2973855 A1 | 10/2016 |
|----|------------|---------|
| EP | 2043729 A2 | 4/2009 |
| WO | 2006135791 A2 | 12/2006 |

OTHER PUBLICATIONS

European Communication pursuant to Article 94(3) EPC from counterpart European Patent Application No. 18724640.0, dated Oct. 21, 2020, 7 pp.
(Continued)

*Primary Examiner* — Catherine M Voorhees
(74) *Attorney, Agent, or Firm* — Shumaker & Sieffert, P.A.

(57) ABSTRACT

Techniques for delivery of electrical neurostimulation therapy to a patient are disclosed. In one example, a processor controls delivery of electrical neurostimulation therapy to a patient by an electrical neurostimulation therapy device and via a plurality of combinations of a plurality of electrodes disposed along a lead inserted across an anatomical midline of a spinal cord of the patient and angled relative to the anatomical midline, the lead connected to the electrical neurostimulation therapy device. The processor determines, based on the electrical neurostimulation therapy, a location of a physiological midline of the spinal cord. The processor selects, based on the location of the physiological midline, at least one electrode of the plurality of electrodes for subsequent delivery of electrical neurostimulation therapy to the patient. Further, the processor displays a representation of the physiological midline and the anatomical midline relative to the spinal cord.

16 Claims, 11 Drawing Sheets

(51) Int. Cl.
*A61N 1/372* (2006.01)
*G16H 20/30* (2018.01)

(52) U.S. Cl.
CPC ..... *A61N 1/36139* (2013.01); *A61N 1/37241* (2013.01); *A61N 1/36071* (2013.01); *G16H 20/30* (2018.01)

(56) References Cited

U.S. PATENT DOCUMENTS

| | | | |
|---|---|---|---|
| 8,744,591 B2 | 6/2014 | Davis et al. | |
| 10,398,899 B2 | 9/2019 | Torgerson | |
| 2008/0228525 A1 | 9/2008 | Mironer | |
| 2010/0305660 A1* | 12/2010 | Hegi ............... | A61N 1/36071 607/60 |
| 2012/0083857 A1 | 4/2012 | Bradley et al. | |
| 2012/0265268 A1* | 10/2012 | Blum ............... | A61N 1/36021 607/46 |
| 2014/0039575 A1 | 2/2014 | Bradley | |
| 2014/0081354 A1 | 3/2014 | Davis et al. | |
| 2014/0236257 A1 | 8/2014 | Parker et al. | |
| 2015/0119957 A1 | 4/2015 | Ranu | |
| 2016/0303376 A1 | 10/2016 | Dinsmoor et al. | |
| 2017/0281958 A1 | 10/2017 | Carmona et al. | |

OTHER PUBLICATIONS

International Preliminary Report on Patentability from counterpart International Application No. PCT/US2018/027270, dated Dec. 30, 2019, 9 pp.

Mironer, MD, et al., "A New Technique of 'Midline Anchoring' in Spinal Cord Stimulation Dramatically Reduces Lead Migration," International Neuromodulation Society, vol. 7, No. 1, Jan. 2004, pp. 32-37.

Mironer, MD, et al., "Efficacy of a Single, Percutaneous, Across Midline, Octrode Lead Using a 'Midline Anchoring' Technique in the Treatment of Chronic Low Back and/or Lower Extremity Pain: A Retrospective Study," Neuromodulation: The Technology at the Nueral Interface, vol. 11, No. 4, Oct. 2008, 10 pp.

Mironer, MD., et al., "Prospective, Two-part Study of the Interaction Between Spinal Cord Stimulation and Peripheral Nerve Field Stimulation in Patients with Low Back Pain: Development of a New Spinal-Peripheral Neurostimulation Method," Neuromodulation 2011; 14: first revision Jun. 4, 2010, pp. 151-155.

Russo, MD et al., "10-kHz High-Frequency SCS Therapy: A Clinical Summary," Pain Medicine Nov. 2014; pp. 934-942.

International Search Report and Written Opinion from International Application No. PCT/US2018/027270, dated Aug. 21, 2018, 15 pp.

Prosecution History from U.S. Appl. No. 15/639,126, dated Sep. 18, 2018 through Apr. 25, 2019, 93 pp.

Response to European Communication pursuant to Article 94(3) EPC from counterpart European Patent Application No. 18724640.0, dated Oct. 21, 2020, filed Feb. 24, 2021, 23 pp.

Summons to attend oral proceedings pursuant to Rule 115(1) EPC from counterpart European Application No. 18724640.0, dated Apr. 30, 2021, 11 pp.

\* cited by examiner

USER INTERFACE FOR IDENTIFYING MIDLINES OF SPINAL CORD

This application is a continuation of U.S. patent application Ser. No. 15/639,126, which was filed on Jun. 30, 2017, and is entitled, "USER INTERFACE FOR IDENTIFYING MIDLINES OF SPINAL CORD." The entire content of U.S. patent application Ser. No. 15/639,126 is incorporated herein by reference.

TECHNICAL FIELD

This disclosure generally relates to systems for electrical neurostimulation of a patient.

BACKGROUND

Electrical neurostimulation therapy, e.g., for pain relief, may be delivered by one or more electrodes positioned along one or more leads inserted into a patient. Positioning of the leads is important to effectively deliver therapy to target site of the patient. Ideally, in the case of spinal cord stimulation (SCS) for pain relief, the leads should be placed on either side of a physiological midline of a spinal cord of the patient (e.g., a conceptual midline wherein electrical neurostimulation delivered to the left of the physiological midline provides pain relief to only a left side of the body of the patient, while electrical neurostimulation delivered to the right of the physiological midline provides pain relief to only a right side of the body of the patient). Typically, a physician uses a fluoroscope to place a first lead parallel and left of an anatomical midline of the spinal cord (e.g., a line bisecting the spinal cord into two lateral sections) and a second lead parallel and right of the anatomical midline of the spinal cord. However, the physiological midline only roughly correlates to the anatomical midline of the spinal cord, and may differ by several millimeters. After implanting the leads, the clinician, while still in the operating room, tests various electrodes combinations among the two leads and the patient provides feedback as to where the patient feels paresthesia or reduction of pain. This process is time consuming and may be inaccurate as the patient suffers disorientation from anesthesia.

SUMMARY

In general, the disclosure describes techniques for more accurately delivering electrical neurostimulation to a spinal cord of a patient. In one example, a clinician implants at least one lead at an angle relative to and across an anatomical midline of a spinal cord of the patient. In some examples, the at least one lead is implanted at an angle of 5-20 degrees relative to the anatomical midline of the spinal cord. In some examples of the techniques disclosed herein, the clinician implants a first and second lead angled 5-20 degrees relative to and across the anatomical midline of the spinal cord. In alternate examples, the first lead is implanted parallel to and offset from the anatomical midline of the spinal cord, while the second lead is implanted at an angle of 5-20 degrees relative to and across the anatomical midline of the spinal cord. Such an implantation procedure as described herein may ensure that at least several electrodes are implanted on either side of the physiological midline of the spinal cord of the patient.

After surgery, and outside of the operating room, the clinician may test various combinations of electrodes to determine the combination that provides the greatest pain relief to the patient. The clinician may use feedback from the patient regarding the different combinations of electrodes to identify a position of the physiological midline of the spinal cord of the patient. The clinician may use a user interface to mark, in reference to the first and second leads, the location of the anatomical midline of the spinal cord via a fluoroscope, and to further mark the location of the physiological midline of the spinal cord via the patient feedback. Accordingly, such an implantation procedure may eliminate the need to perform testing of the implanted electrodes within the operation room, which may reduce the cost of the procedure, increase the reliability of the feedback received from the patient, and eliminate the need to wake the patient up from anesthesia to provide feedback on the electrical neurostimulation therapy, paresthesia, and pain sensations.

In one example, this disclosure describes a method including: controlling, by one or more processors, delivery of electrical neurostimulation therapy to a patient by an electrical neurostimulation therapy device and via a plurality of combinations of a plurality of electrodes, wherein the plurality of electrodes are disposed along a lead inserted across an anatomical midline of a spinal cord of the patient and angled relative to the anatomical midline of the spinal cord, the lead connected to the electrical neurostimulation therapy device; determining, based on the delivery of the electrical neurostimulation therapy, a location of a physiological midline of the spinal cord of the patient; selecting, based on the location of the physiological midline of the spinal cord, at least one electrode of the plurality of electrodes for subsequent delivery of electrical neurostimulation therapy to the patient; and controlling, by the one or more processors, delivery of electrical neurostimulation therapy to the patient by the electrical neurostimulation therapy device and via the selected at least one electrode of the plurality of electrodes.

In another example, this disclosure describes an electrical neurostimulation therapy system including: a plurality of electrodes disposed along a lead inserted across an anatomical midline of a spinal cord of a patient and angled relative to the anatomical midline of the spinal cord, the lead connected to an electrical neurostimulation therapy device; a therapy delivery circuit of the electrical neurostimulation therapy device configured to deliver electrical neurostimulation therapy to the patient via a plurality of combinations of the plurality of electrodes; and one or more processors configured to: control delivery of the electrical neurostimulation therapy to the patient; determine, based on the delivery of the electrical neurostimulation therapy, a location of a physiological midline of the spinal cord of the patient; based on the location of the physiological midline of the spinal cord of the patient, select at least one electrode of the plurality of electrodes for subsequent delivery of electrical neurostimulation therapy to the patient; and control delivery of electrical neurostimulation therapy to the patient by the electrical neurostimulation therapy device and via the selected at least one electrode of the plurality of electrodes In another example, this disclosure describes an electrical neurostimulation therapy system including: a plurality of electrodes disposed along a lead inserted across an anatomical midline of a spinal cord of a patient and angled relative to the anatomical midline of the spinal cord, the lead connected to an electrical neurostimulation therapy device; a therapy delivery circuit of the electrical neurostimulation therapy device configured to deliver electrical neurostimulation therapy to the patient via a plurality of combinations of the plurality of electrodes; and one or more processors configured to: control delivery of the electrical neurostimulation therapy to the patient; determine, based on the delivery of the electrical neurostimulation therapy, a location of a physiological midline of the spinal cord of the patient; and present, for display to a user, a representation of the spinal cord, the location of the physiological midline of the spinal cord relative to the spinal cord, and a location of an anatomical midline of the spinal cord relative to the spinal cord.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

Like reference characters refer to like elements throughout the figures and description.

DETAILED DESCRIPTION

Figure 1:
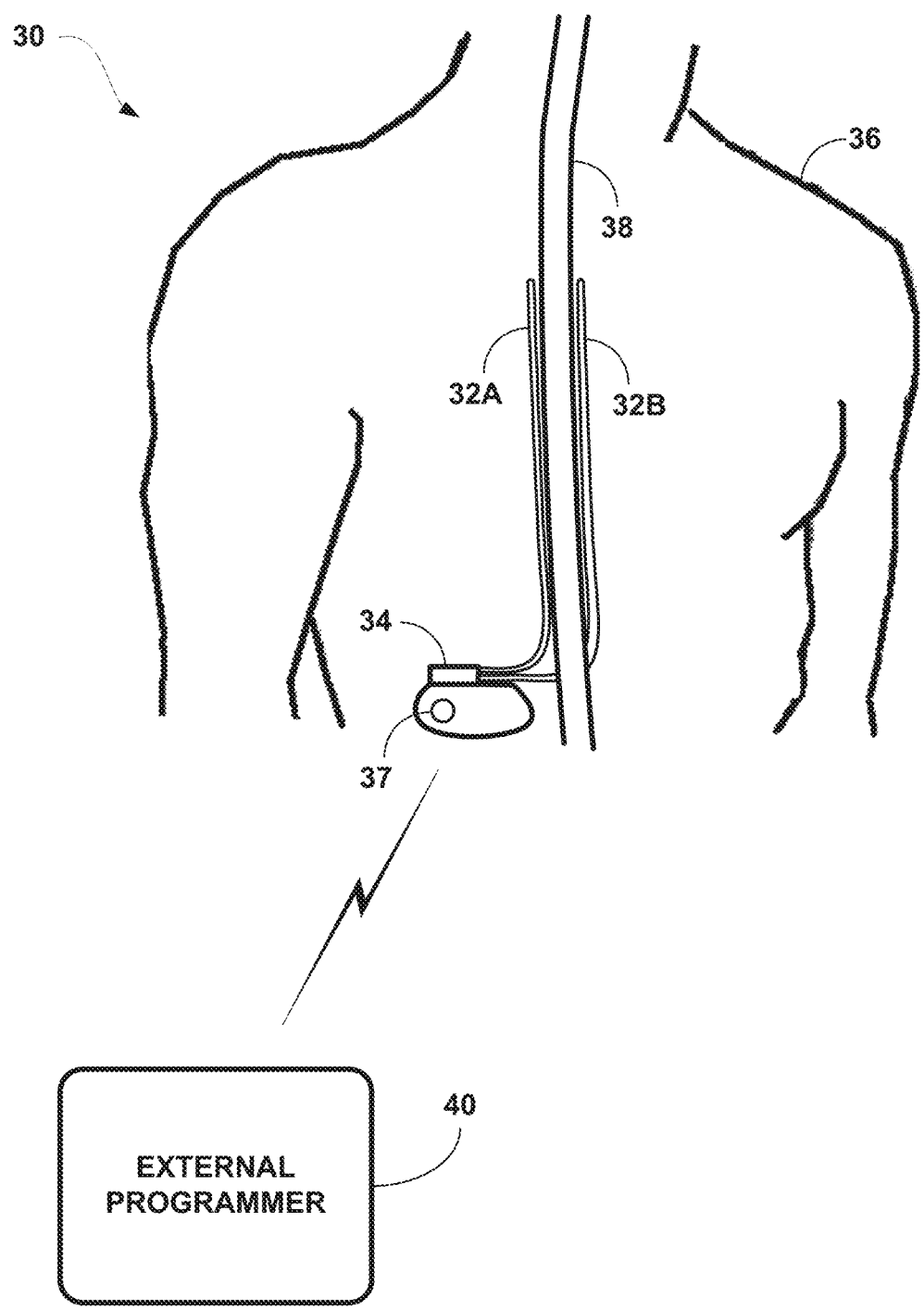
FIG. 1 is a conceptual diagram illustrating an example system that delivers stimulation therapy to a spinal cord of a patient in accordance with the techniques of the disclosure.

FIG. 1 is a conceptual diagram illustrating system 30 that delivers stimulation therapy to spinal cord 38 of patient 36 in accordance with the techniques of the disclosure. System 30 delivers electrical neurostimulation therapy from implantable stimulator 34 to spinal cord 38 via one or more electrodes (not shown) carried by, i.e., located on, implantable medical leads 32A and 32B (collectively "leads 32") as well as the housing of implantable stimulator 34, e.g., housing electrode 37. System 30 and, more particularly, implantable stimulator 34, may operate in in a current-based or voltage-based configuration. That is, in a current-based example, implantable stimulator 34 delivers controlled current stimulation pulses or waveforms to patient 36 via one or more regulated, stimulation electrodes. Alternatively, in a voltage-based example, implantable stimulator 34 may be configured to deliver constant voltage pulses. Various parameters of the pulses or waveforms may be defined by one or more stimulation programs. The pulses or waveforms may be delivered substantially continuously or in bursts, segments, or patterns, and may be delivered alone or in combination with pulses or waveforms defined by one or more other stimulation programs. In some example, implantable stimulator 34 delivers spinal cord stimulation (SCS) therapy to patient 36 via the electrodes carried by, i.e., located on, leads 32 to provide pain relief therapy to patient 36.

Stimulator 34 may be implanted in patient 36 at a location minimally noticeable to the patient. For SCS, stimulator 34 may be located in the lower abdomen, lower back, or other location to secure the stimulator. Leads 32 may be tunneled from stimulator 34 through tissue to reach the target tissue adjacent to spinal cord 38 for stimulation delivery. At the distal ends of leads 32 are one or more electrodes (not shown) that transfer the stimulation pulses from the lead to the tissue substantially simultaneously with stimulation pulses.

In the example of FIG. 1, the distal ends of leads 32 are placed adjacent to the target tissue of spinal cord 38. The proximal ends of leads 32 may be both electrically and mechanically coupled to implantable stimulator 34 either directly or indirectly via a lead extension and header. Alternatively, in some examples, leads 32 may be implanted and coupled to an external stimulator, e.g., through a percutaneous port. In additional example implementations, stimulator 34 may be a leadless stimulator with one or more arrays of electrodes arranged on a housing of the stimulator rather than leads that extend from the housing.

Application of certain techniques will be described in this disclosure with respect to implantable stimulator 34 and implantable leads 32 having ring electrodes for purposes of illustration. Ring electrodes are commonly used in electrical neurostimulation applications because they are simple to program and are capable of delivering an electrical field to any tissue adjacent to leads 32. However, other types of electrodes may be used. For example, the electrodes of leads 32 may have a complex electrode array geometry that is capable of producing shaped electrical fields. The complex electrode array geometry may include multiple electrodes (e.g., partial ring or segmented electrodes) around the perimeter of each lead 32, rather than one ring electrode. In this manner, electrical stimulation may be directed in a specific direction from leads 32 to enhance therapy efficacy and reduce possible adverse side effects from stimulating a large volume of tissue. In alternative examples, leads 32 may have shapes other than elongated cylinders as shown in FIG. 1. For example, leads 32 may be electrode pads on a paddle lead, circular (i.e., ring) electrodes surrounding the body of leads 32, spherical leads, bendable leads, conformable electrodes, cuff electrodes, segmented electrodes, or any other type of electrodes capable of forming unipolar, bipolar or multi-polar electrode configurations and effective in treating patient 36. In some examples, one or more of the electrodes may be unregulated. In some examples, the housing of implantable stimulator 34, e.g., housing electrode 37, functions as an anode and/or return path for the electrical stimulation.

The stimulation pulses may be delivered using various electrode arrangements such as unipolar arrangements, bipolar arrangements or multipolar arrangements. A unipolar stimulation arrangement generally refers to the use of an anode on the housing that sources current and one or more cathodes on one or more leads that sink current. A bipolar stimulation arrangement generally refers to the use of an anode on a lead that sources current and a cathode on the same lead and/or another lead that sink current. A multipolar stimulation arrangement generally refers to the use of more than one anode on a lead that each source current and one or more cathodes on the same lead or another lead that sink current, or the use of one anode on a lead that sources current and multiple cathodes on the same lead or another lead that sink current. A hybrid stimulation arrangement that combines both unipolar and bipolar electrode relationships may be referred to as an omnipolar arrangement. In an omnipolar arrangement, an anode on the housing may be used to deliver stimulation pulses substantially simultaneously with at least one anode on a lead and at least one cathode on a lead. In this case, for an omnipolar arrangement, at least one anode on a lead and at least one anode on the housing can be used simultaneously in combination with at least one cathode on a lead. In other omnipolar arrangements, a cathode on the housing may be used to deliver stimulation pulses substantially simultaneously with at least one cathode on a lead and at least one anode on a lead. In this alternative case, for an omnipolar arrangement, at least one cathode on a lead and at least one cathode on the housing can be used simultaneously in combination with at least one anode on a lead. Any of the above electrode arrangements, or other electrode arrangements, may be used to deliver electrical stimulation in accordance with techniques described in this disclosure.

Implantable stimulator 34 delivers stimulation to spinal cord 38 to reduce the amount of pain perceived by patient 36. The stimulation delivered by implantable stimulator 34 may take the form of stimulation pulses or continuous stimulation waveforms, and may be characterized by controlled current or voltage levels, as well as programmed pulse widths and pulse rates in the case of stimulation current pulses. Stimulation may be delivered via selected combinations of electrodes located on one or both of leads 32 and on the housing. Stimulation of spinal cord 38 may, for example, prevent pain signals from traveling through the spinal cord and to the brain of the patient. Patient 34 perceives the interruption of pain signals as a reduction in pain and, therefore, efficacious therapy.

In some examples, therapy system 30 further includes external programmer 40. External programmer 40 may be used to define stimulation therapy parameters for use by implantable stimulator 34. In some examples, programmer 40 is a clinician programmer, which is a handheld computing device that permits a clinician to program stimulation therapy for patient 36 via a user interface, e.g., using input keys and a display. For example, using the clinician programmer, the clinician may specify stimulation parameters, i.e., create programs, for use in delivery of stimulation therapy. The clinician programmer may support telemetry (e.g., radio frequency (RF) telemetry) with implantable stimulator 34 to download programs and, optionally, upload operational or physiological data stored by implantable stimulator 34. In this manner, the clinician may periodically interrogate implantable stimulator 34 to evaluate efficacy and, if necessary, modify the programs or create new programs. In some examples, the clinician programmer transmits programs to a patient programmer (not depicted) in addition to or instead of implantable stimulator 34. In some examples, the patient programmer may serve as the clinician programmer.

In other examples, external programmer 40 is a patient programmer. Like the clinician programmer, the patient programmer may be a handheld computing device. The patient programmer may also include a display and input keys to allow patient 36 to interact with the patient programmer and implantable stimulator 34. In this manner, the patient programmer provides patient 36 with a user interface for control of the stimulation therapy delivered by implantable stimulator 34. For example, patient 36 may use the patient programmer to start, stop or adjust electrical stimulation therapy. In particular, the patient programmer may permit patient 36 to adjust stimulation parameters of a program such as duration, current or voltage amplitude, pulse width and pulse rate. Patient 36 may also select a program, e.g., from among a plurality of stored programs, as the present program to control delivery of stimulation by implantable stimulator 34.

With reference to FIG. 1, a user, such as a clinician or patient 36, may interact with a user interface of external programmer 40 to program stimulator 34. Programming of stimulator 34 may refer generally to the generation and transfer of commands, programs, or other information to control the operation of the stimulator. For example, programmer 40 may transmit programs, parameter adjustments, program selections, group selections, or other information to control the operation of stimulator 34, e.g., by wireless telemetry. In accordance with this disclosure, programmer 40 may transmit to the stimulator 34 information regarding the patient and regarding therapy the patient received during previous sessions including, for example, images that show placement of leads 32.

Whether programmer 40 is configured for clinician or patient use, programmer 40 may communicate to implantable stimulator 34 or any other computing device via wireless communication. Programmer 40, for example, may communicate via wireless communication with implantable stimulator 34 using radio frequency (RF) telemetry techniques known in the art or other communication standards such as, for example, Bluetooth®. Programmer 40 may also communicate with another programmer or computing device via a wired or wireless connection using any of a variety of local wireless communication techniques, such as RF communication according to the 802.11 or Bluetooth® specification sets, infrared communication according to the IRDA specification set, or other standard or proprietary telemetry protocols. Programmer 40 may also communicate with another programming or computing device via exchange of removable media, such as magnetic or optical disks, or memory cards or sticks. Further, programmer 40 may communicate with implantable stimulator 34 and other programming devices via remote telemetry techniques known in the art, communicating via a local area network (LAN), wide area network (WAN), public switched telephone network (PSTN), or cellular telephone network, for example.

Implantable stimulator 34, and external programmer 40 may communicate via cables or a wireless communication, as shown in FIG. 1. External programmer 40 may, for example, communicate via wireless communication with implantable stimulator 34 using RF telemetry techniques known in the art or other standard communication protocols such as, for example, Bluetooth®. External programmer 40 also may communicate with each other using any of a variety of wireless communication techniques, such as RF communication according to the 802.11 or Bluetooth® specification sets, infrared communication, e.g., according to the IrDA standard, or other standard or proprietary telemetry protocols. External programmer 40 may include a transceiver to permit bi-directional communication with implantable stimulator 34.

According to the techniques of the disclosure, a clinician implants at least one lead 32 at an angle relative to and across an anatomical midline of spinal cord 38 of patient 36. In some examples, the at least one lead 32 is implanted at an angle of 5-20 degrees relative to the anatomical midline of spinal cord 38 of patient 36. In some examples of the techniques disclosed herein, the clinician implants a first lead 32A and second lead 32B angled 5-20 degrees relative to and across the anatomical midline of spinal cord 38. In alternate examples, the first lead 32A is implanted parallel to and offset from the anatomical midline of spinal cord 38, while the second lead 32B is implanted at an angle of 5-20 degrees relative to and across the anatomical midline of spinal cord 38. Such an implantation procedure as described herein may ensure that at least several electrodes are implanted on either side of the physiological midline of spinal cord 38.

After surgical implantation of stimulator 34, and outside of the operating room, the clinician may test various combinations of electrodes to determine the combination that provides the greatest pain relief to the patient. The clinician may use feedback from the patient regarding the different combinations of electrodes to identify a position of the physiological midline of spinal cord 38. The clinician may use a user interface to mark, in reference to the first and second leads, the location of the anatomical midline of spinal cord 38 via a fluoroscope, and to further mark the location of the physiological midline of spinal cord 38 via the patient feedback. Accordingly, such an implantation procedure may eliminate the need to perform testing of the implanted electrodes within the operation room, which may reduce the cost of the procedure, increase the reliability of the feedback received from the patient, and eliminate the need to wake the patient up from anesthesia to provide feedback on the electrical neurostimulation therapy, paresthesia, and pain sensations.

Figure 2:
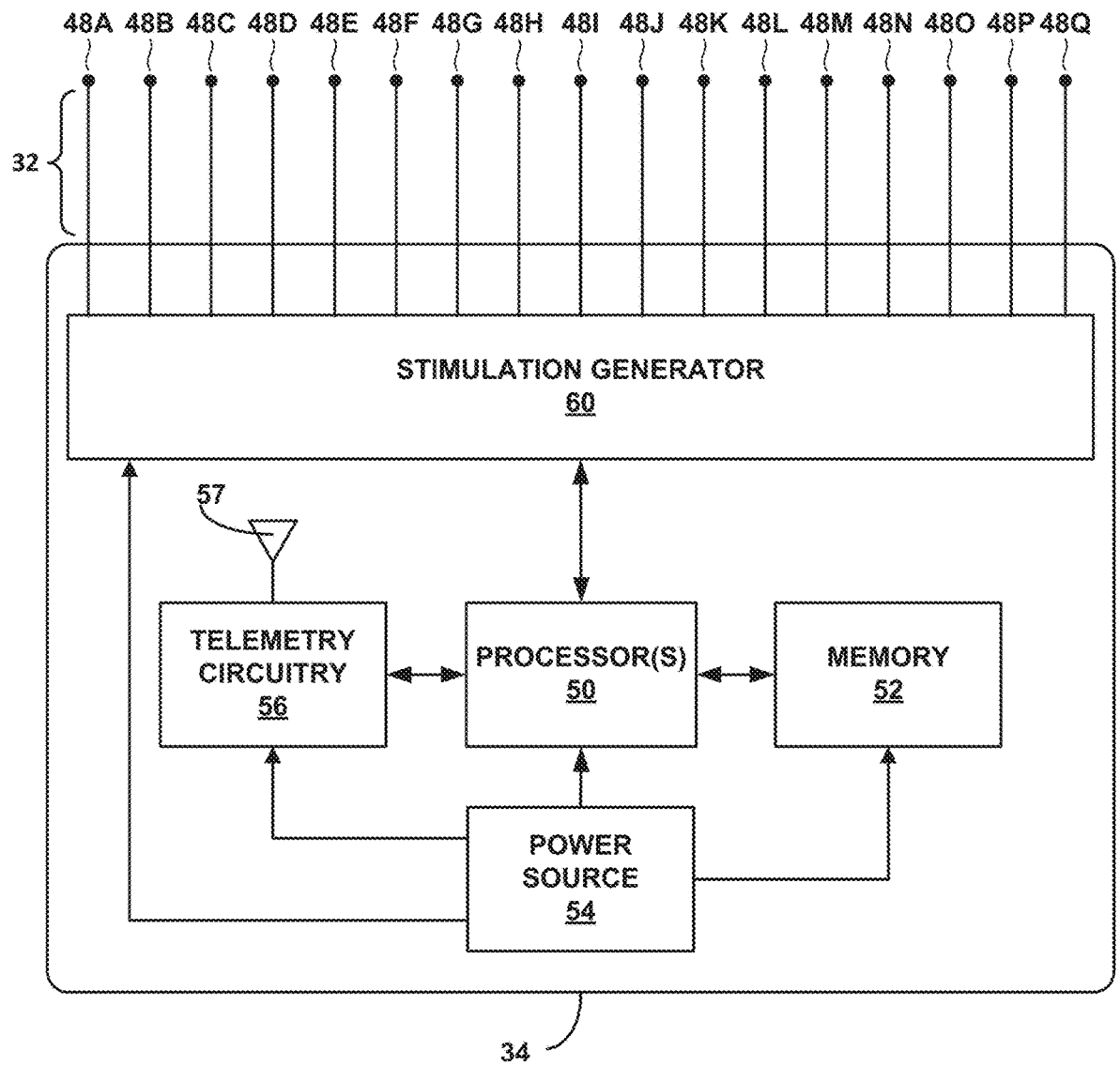
FIG. 2 is a block diagram illustrating various example components of an implantable electrical stimulator of a system in accordance with the techniques of the disclosure.

FIG. 2 is a block diagram illustrating various components of an example implantable stimulator 34 of system 30 in accordance with the techniques of the disclosure. In the example of FIG. 2, implantable stimulator 34 includes processor 50, memory 52, power source 54, telemetry circuitry 56, antenna 57, and a stimulation generator 60. Implantable stimulator 34 is also shown in FIG. 2 coupled to electrodes 48A-Q (collectively "electrodes 48"). Electrodes 48A-48P are implantable and may be deployed on one or more implantable leads 32. With respect to FIG. 1, lead 32A and 32B may carry electrodes 48A-H and electrodes 48I-P, respectively. In some cases, one or more additional electrodes may be located on or within the housing of implantable stimulator 34, e.g., to provide a common or ground electrode or a housing anode. With respect to FIG. 2, leads 32A and 32B may carry electrodes 48A-H and electrodes 48I-P, respectively. In the examples of FIGS. 1 and 2, a lead or lead segment carries eight electrodes to provide a 2×8 electrode configuration (two leads with 8 electrodes each), providing a total of sixteen different electrodes. The leads may be detachable from a housing associated with implantable stimulator 34, or be fixed to such a housing.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), one lead with 12 electrodes (1×12), one lead with 16 electrodes (1×16), two leads with four electrodes each (2×4), three leads with four electrodes each (3×4), three leads with eight electrodes each (3×8), three leads with four, eight, and four electrodes, respectively (4-8-4), two leads with 12 or 16 electrodes (2×12, 2×16), two or more leads with 11 or 13 electrodes, or other configurations. Different electrodes are selected to form electrode combinations. Polarities are assigned to the selected electrodes to designate the electrodes as anodes or cathodes and form electrode configurations.

Electrode 48Q represents one or more electrodes that may be carried on a housing, i.e., can, of implantable stimulator 34. e.g., housing electrode 37 of FIG. 1. Electrode 48Q may also be a dedicated short lead extending from the housing, or a proximal portion of one of the leads carrying electrodes 48A-48P. The proximal portion may be closely adjacent to the housing, e.g., at or near a point at which a lead is coupled to the housing, such as adjacent to a lead connection header 8 of the housing. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of implantable stimulator 34, such as stimulation generator 60, processor 50, memory 52, telemetry circuitry 56, and power source 54.

Housing electrode 48Q may be configured for use as an anode to source current substantially simultaneously with one or more electrodes 48A-48P configured for use as cathodes sinking current in a unipolar arrangement. Housing electrode 48Q may be configured for use as an anode to source current substantially simultaneously with current sourced by another electrode 48A-48P configured for use as an anode in an omnipolar arrangement. By way of specific example, electrodes 48A, 48B, and housing electrode 48Q each could be configured for use as anodes. Electrodes 48A, 48B could deliver electrical stimulation current substantially simultaneously with the electrical stimulation current delivered via housing electrode 48Q. In this illustration, one or more cathodes could be formed with other electrodes (e.g., any of electrodes 48C-48P) on the leads to sink current sourced by anodes 48A, 48B and 48Q.

Memory 52 may store instructions for execution by processor 50, stimulation therapy data, sensor data, and/or other information regarding therapy for patient 36. Processor 50 may control stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 34 in this disclosure.

Processor 50 may include one or more microprocessors, digital signal processors (DSPs), application-specific integrated circuits (ASICs), field-programmable gate arrays (FPGAs), or other digital logic circuitry. Processor 50 controls operation of implantable stimulator 34, e.g., controls stimulation generator 60 to deliver stimulation therapy according to a selected program or group of programs retrieved from memory 52. For example, processor 50 may control stimulation generator 60 to deliver electrical signals, e.g., as stimulation pulses or continuous waveforms, with current amplitudes, pulse widths (if applicable), and rates specified by one or more stimulation programs. Processor 50 may also control stimulation generator 60 to selectively deliver the stimulation via subsets of electrodes 48, also referred to as electrode combinations, and with polarities specified by one or more programs.

Upon selection of a particular program group, processor 50 may control stimulation generator 60 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and regulated/unregulated status of the electrodes. The electrode combination may specify particular electrodes in a single array or multiple arrays, and on a single lead or among multiple leads. The electrode combination may include at least one anode on the housing of the IMD, e.g., electrode 48Q, at least one anode on a lead, electrode 48A, and at least one cathode on a lead. The lead-borne anode and cathode may be on the same lead or different leads, if more than one lead is provided. A program may be defined directly, by selecting parameters and electrodes, or by zone-based programming, in which parameters and electrodes are automatically determined by the programmer in response to manipulation or positioning of stimulation zones.

Stimulation generator 60 is electrically coupled to electrodes 48A-P via conductors of the respective lead, such as lead 12 in FIG. 1 or leads 32 in FIG. 2, in implementations in which electrodes 48A-P are carried by, located on, leads. Stimulation generator 60 may be electrically coupled to one or more housing ("can") electrodes 48Q via an electrical conductor disposed within the housing of implantable stimulator 34 of FIG. 1 or FIG. 2. Housing electrode 48Q may be configured as a regulated or unregulated electrode to form an electrode configuration in conjunction with one or more of electrodes 48A-48P located on leads of the IMD. Housing electrode 48Q may be configured for use as an anode to source current substantially simultaneously with one or more electrodes, e.g., any of electrodes 48A-48P, on one or more leads configured for use as anodes.

Stimulation generator 60 may include stimulation generation circuitry to generate stimulation pulses or waveforms and circuitry for switching stimulation across different electrode combinations, e.g., in response to control by processor 50. Stimulation generator 60 produces an electrical stimulation signal in accordance with a program based on control signals from processor 50.

For example, stimulation generator 60 may include a charging circuit that selectively applies energy from power source 54 to a capacitor module for generation and delivery of a supply voltage for generation of stimulation signal. In addition to capacitors, the capacitor module may include switches. In this manner, the capacitor module may be configurable, e.g., based on signals from processor 50, to store a desired voltage for delivery of stimulation at a voltage or current amplitude specified by a program. For delivery of stimulation pulses, switches within the capacitor module may control the widths of the pulses based on signals from processor 50.

In one example implementation, e.g., an omnipolar arrangement, stimulation generator 60 may be configured to deliver stimulation using one or more of electrodes 48A-P as stimulation electrodes, e.g., anodes, while substantially simultaneously delivering stimulation using housing electrode 48Q as a stimulation electrode, e.g., anode. The anodes on the lead(s) and the housing may be used to deliver stimulation in conjunction with one or more cathodes on the lead(s). As one illustration, an electrode combination selected for delivery of stimulation current may comprise an anode on the IMD housing, and anode on a lead, and a cathode on the same lead or a different lead. In other examples, the electrode combination may include multiple anodes and/or multiple cathodes on one or more leads in conjunction with at least one anode on the IMD housing. In some examples, the electrode combination may include one or more anodes on one or more leads, and one or more cathodes on the same lead or a different lead, e.g., a bipolar/multipolar arrangement. In other examples, the electrode combination may include an anode on the housing, and one or more cathodes on one or more leads, e.g., omnipolar arrangement. In yet another example, the electrode combination may include a cathode on the housing, and one or more additional cathodes on one or more leads, along with one or more anodes also on the leads, e.g., a variation of an omnipolar arrangement.

Telemetry circuitry 56 may include a radio frequency (RF) transceiver to permit bi-directional communication between implantable stimulator 34 and each of clinician programmer 20 and patient programmer 22. Telemetry circuitry 56 may include an antenna 57 that may take on a variety of forms. For example, antenna 57 may be formed by a conductive coil or wire embedded in a housing associated with implantable stimulator 34. Alternatively, antenna 57 may be mounted on a circuit board carrying other components of implantable stimulator 34 or take the form of a circuit trace on the circuit board. In this way, telemetry circuitry 56 may permit communication with clinician programmer 40 and patient programmer 22 in FIG. 1 or external programmer 40 in FIG. 2, to receive, for example, new programs or program groups, or adjustments to programs or program groups.

Power source 54 may be a non-rechargeable primary cell battery or a rechargeable battery and may be coupled to power circuitry. However, the disclosure is not limited to implementations in which the power source is a battery. In another example, as an example, power source 54 may comprise a supercapacitor. In some examples, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional embodiments, power source 54 may include a small rechargeable circuit and a power generation circuit to produce the operating power. Recharging may be accomplished through proximal inductive interaction between an external charger and an inductive charging coil within stimulator 34. In some embodiments, power requirements may be small enough to allow stimulator 34 to utilize patient motion at least in part and implement a kinetic energy-scavenging device to trickle charge a rechargeable battery. A voltage regulator may generate one or more regulated voltages using the battery power.

According to the techniques of the disclosure, a clinician implants at least one lead 32 at an angle relative to and across an anatomical midline of spinal cord 38 of patient 36. In some examples, the at least one lead 32 is implanted at an angle of 5-20 degrees relative to the anatomical midline of spinal cord 38 of patient 36. In some examples of the techniques disclosed herein, the clinician implants a first lead 32A and second lead 32B angled 5-20 degrees relative to and across the anatomical midline of spinal cord 38. In alternate examples, the first lead 32A is implanted parallel to and offset from the anatomical midline of spinal cord 38, while the second lead 32B is implanted at an angle of 5-20 degrees relative to and across the anatomical midline of spinal cord 38. Such an implantation procedure as described herein may ensure that at least several electrodes are implanted on either side of the physiological midline of spinal cord 38.

After surgical implantation of stimulator 34, and outside of the operating room, the clinician may test various combinations of electrodes 48 to determine the combination that provides the greatest pain relief to the patient. For example, in response to commands from external programmer 40, processor 50 may control stimulation generator 60 to deliver electrical neurostimulation to patient 36 via a plurality of combinations of electrodes 48. The clinician may use feedback from the patient regarding the plurality of combinations of electrodes 48 to identify a position of the physiological midline of spinal cord 38. The clinician selects, based on the location of the physiological midline of spinal cord 38, at least one electrode of the plurality of electrodes for subsequent delivery of electrical neurostimulation therapy to the patient. Processor 50 controls stimulation generator 60 to deliver electrical neurostimulation to patient 36 according to the selected at least one electrode of the plurality of electrodes to provide pain relief therapy to patient 36.

Figure 3:
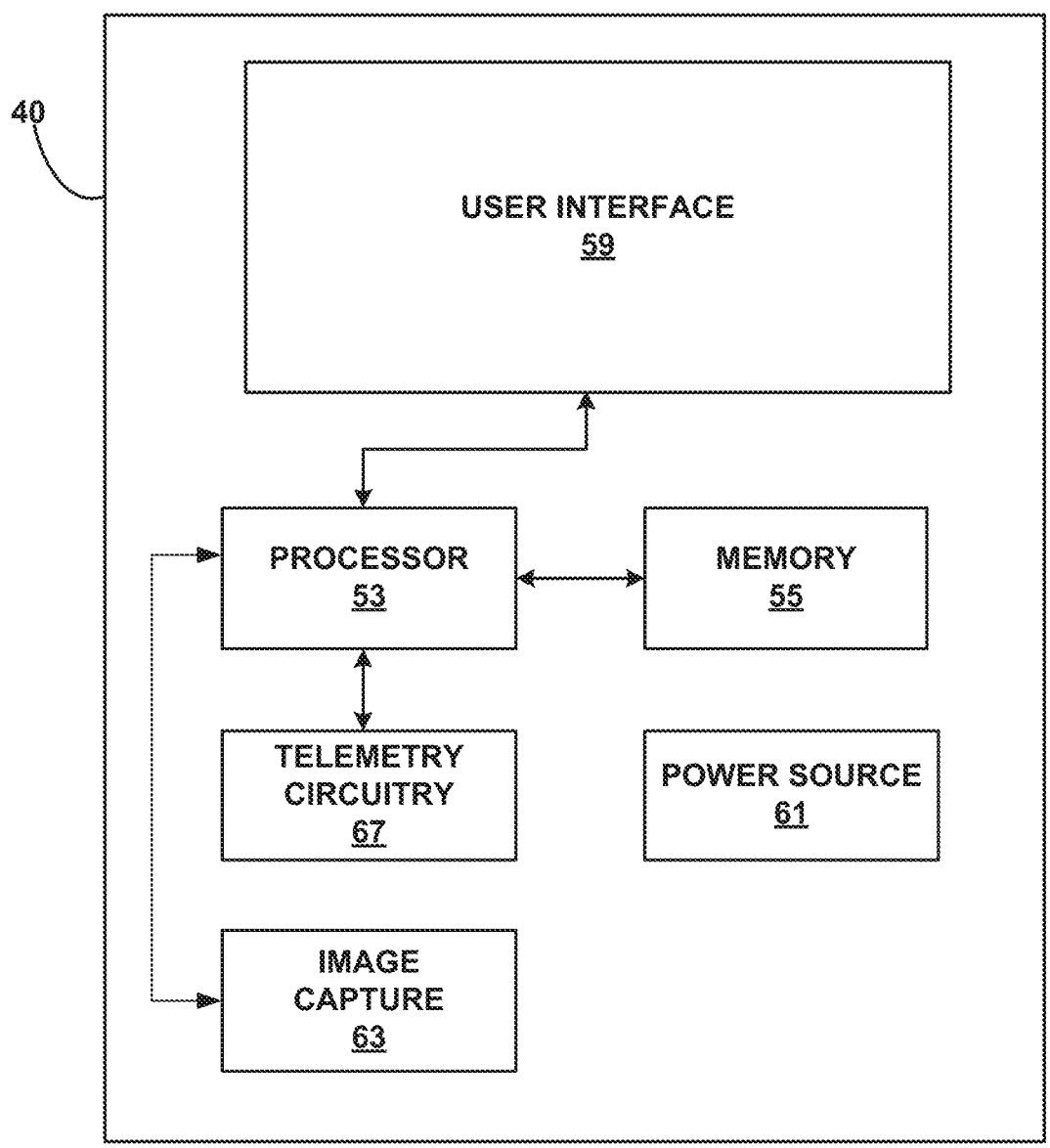
FIG. 3 is a functional block diagram illustrating various components of an external programmer for an implantable stimulator.

FIG. 3 is a functional block diagram illustrating various components of an external programmer 40 for an implantable stimulator 34. External programmer 40 of FIG. 3 may be a clinician programmer or a patient programmer. External programmer 40 includes processor 53, memory 55, telemetry module 67, user interface 59, and power source 61. In general, processor 53 controls user interface 59, stores and retrieves data to and from memory 55, and controls transmission of data with implantable stimulator 34 through telemetry module 67. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 55 may store instructions that cause processor 53 to provide various aspects of the functionality ascribed to external programmer 40 herein. Memory 55 may include any fixed or removable magnetic, optical, or electrical media, such as RAM. ROM, CD-ROM, magnetic disks, EEPROM, or the like. Memory 55 may also include a removable memory portion that may be used to provide memory updates or increases in memory capacities. A removable memory may also allow patient data to be easily transferred to another computing device, or to be removed before programmer 40 is used to program therapy for another patient. Memory 55 may also store information that controls operation of implantable stimulator 34, such as therapy delivery values.

In some examples, external programmer 40 includes an image capturing device 63. The image capturing device 63 may be built into the external programmer 40 or may be connected to the external programmer 40 via an interface using a wired or wireless connection. The processor 53 may control the image capturing device 63 to capture images as specified by the user of the external programmer 40. In some examples, image capturing device 63 may be a digital camera or web camera integrated with or coupled to programmer 40 to capture digital photographs of images presented on hardcopy media, such as film or paper, or a digital image display screen. Alternatively, the programmer may obtain the image electronically from an imaging device, a network storage server, a removable storage medium such as Flash memory, or other devices, directly or over a network.

A clinician or patient 36 interacts with user interface 59 in order to, for example, manually select, change, or modify programs, e.g., by adjusting voltage or current amplitude, adjusting pulse rate, adjusting pulse width, or selecting different electrode combinations or configurations, and may provide efficacy feedback, or view stimulation data. User interface 59 may include a screen and one or more input buttons that allow external programmer 40 to receive input from a user. The screen may be, for example, a liquid crystal display (LCD), plasma display, organic light emitting diode (OLED), electrophoretic displays, dot matrix display, or touch screen. The input buttons may include a touch pad, increase and decrease buttons, emergency shut off button, and other input media needed to control the stimulation therapy.

Using the techniques of this disclosure, a clinician or patient 36 may graphically define desired stimulation regions using interface 59, and may capture an image of the stimulated regions and the placement of the leads that stimulate the regions using the image capturing device 63. The clinician or patient 36 may utilize, for example, the user interface 59 to control the image capturing device 63 to obtain an image and to manipulate the image, as will be described in more detail below. In one example, the clinician or patient may utilize the image capturing device 63 directly to obtain the image.

Telemetry module 67 allows the transfer of data to and from stimulator 34. Telemetry module 67 may communicate automatically with stimulator 34 at a scheduled time or when the telemetry module detects the proximity of the stimulator. Alternatively, telemetry module 67 may communicate with stimulator 34 when signaled by a user through user interface 59. To support RF communication, telemetry module 44 may include appropriate electronic components, such as amplifiers, filters, mixers, encoders, decoders, and the like. In other examples, telemetry module 67 may employ other communication standards such as, for example, Bluetooth® and telemetry module 67 may include the appropriate Bluetooth® components.

Programmer 40 may communicate wirelessly with implantable stimulator 34 using, for example, RF communication or proximal inductive interaction or other communication standards such as, for example, Bluetooth®. This wireless communication is possible through the use of telemetry module 67 which may be coupled to an internal antenna or an external antenna. Telemetry module 67 may be similar to telemetry module 57 of implantable stimulator 34.

Programmer 40 may also be configured to communicate with another computing device via wireless communication techniques, or direct communication through a wired, e.g., network, connection. Examples of local wireless communication techniques that may be employed to facilitate communication between programmer 40 and another computing device include RF communication based on the 802.11 or Bluetooth® specification sets, infrared communication, e.g., based on the IrDA standard.

Power source 61 delivers operating power to the components of programmer 40. Power source 61 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

According to the techniques of the disclosure, a clinician may, via external programmer 40, test various combinations of electrodes 48 of implantable stimulator 34 to determine the combination that provides the greatest pain relief to the patient. For example, the clinician, via user interface 59 of external programmer 40, may control implantable stimulator 34 to deliver electrical neurostimulation to patient 36 via a plurality of combinations of electrodes 48.

The clinician may use feedback from the patient regarding the plurality of combinations of electrodes 48 to identify a position of the physiological midline of spinal cord 38. For example, upon determining that patient 36 experiences suppression of a pain sensation and/or paresthesia on only a right lateral side of patient 36, the clinician may determine that the electrodes of the electrode combination are located to the right of the physiological midline of spinal cord 38. Further, upon determining that patient 36 experiences suppression of a pain sensation and/or paresthesia on only a left lateral side of patient 36, the clinician may determine that the electrodes of the electrode combination are located to the left of the physiological midline of spinal cord 38. By determining that patient 36 experiences suppression of a pain sensation and/or paresthesia on both a right and a left lateral side of patient 36, the clinician may determine that at some of the electrodes of the electrode combination are located to the left and right of the physiological midline of spinal cord 38, e.g., the physiological midline of spinal cord 38 lies between the electrodes of the electrode combination. The clinician selects, based on the location of the physiological midline of spinal cord 38, at least one electrode of the plurality of electrodes for subsequent delivery of electrical neurostimulation therapy to the patient. In some examples, the clinician selects a combination of electrodes having electrodes positioned to both a left and a right lateral side of the physiological midline.

In some examples, processor 53 determines, based on the delivery of the electrical neurostimulation, a position of the physiological midline of spinal cord 38. For example, processor 53 may monitor a physiological response of a tissue of patient 36 during delivery of a electrical neurostimulation according to a plurality of different electrode combinations. In some examples, the tissue response is an evoked compound action potential (eCAP) response of a nerve fiber of patient 36. In some examples, the eCAP response arises from an external stimulation device, such as a transcutaneous electrical nerve stimulation (TENS) device, on one side of the patient's body. In some examples, the external stimulation device is attached to the patient's leg, buttocks, or one side of the lower back. While the external stimulation device delivers electrical nerve stimulation, electrodes performing eCAP monitoring detect the eCAP signal on that side of the body. In some examples, eCAP monitoring is performed in the operating room. In other examples, the tissue response is a visible muscle twitching response of patient 36.

By determining that a first electrode combination evokes a response on only a right lateral side of patient 36, processor 50 may determine that the electrodes of the first electrode combination are located to the right of the physiological midline of spinal cord 38. Further, by determining that a second electrode combination evokes a response on only a left lateral side of patient 36, processor 53 may determine that the electrodes of the second electrode combination are located to the left of the physiological midline of spinal cord 38. By determining that a third electrode combination evokes a response on both a right and a left lateral side of patient 36, processor 53 may determine that at some of the electrodes of the third electrode combination are located to the left and right of the physiological midline of spinal cord 38, e.g., the physiological midline of spinal cord 38 lies between the electrodes of the third electrode combination. In some examples, processor 50 determines whether a particular electrode combination evokes a response of patient 36 by increasing the magnitude of the electrical stimulation and determining the motor threshold of patient 36 (e.g., the magnitude at which patient 36 experiences muscle contractions) on one side of the body or the other.

Processor 53 selects, based on the location of the physiological midline of spinal cord 38, at least one electrode of the plurality of electrodes for subsequent delivery of electrical neurostimulation therapy to the patient. In some examples, processor 53 selects a combination of electrodes having electrodes positioned to both a left and a right lateral side of the physiological midline (e.g., the third electrode combination in the above example). Processor 53 controls delivery of the electrical neurostimulation via the selected combination of electrodes for pain relief therapy for patient 36.

In some examples, user interface 59 includes a display screen that provides an image of spinal cord 38 of patient 36. In such an example, the clinician provides, via user interface 59, an indication of a location of an anatomical midline of spinal cord 38. Processor 53 stores the location of the anatomical midline in memory 55. Based on the indication of the location of the anatomical midline, processor 53 generates a representation of the anatomical midline of spinal cord 38 relative to the image of spinal cord 38 of patient 36 for display to the clinician via user interface 59. Furthermore, as described above, processor 53 determines a location of the physiological midline of spinal cord 38 or receives, from the clinician, an indication of the location of the physiological midline from the clinician, and processor 53 stores the location of the physiological midline in memory 55. In some examples, processor 53 stores the location of the physiological midline within memory 52 of implantable stimulator 34 together with fluoroscopic imagery data for patient 36. Further, based on the location of the physiological midline of spinal cord 38, processor 53 generates a representation of the physiological midline of spinal cord 38 relative to the image of spinal cord 38 of patient 36 for display to the clinician via user interface 59.

Figure 4A:
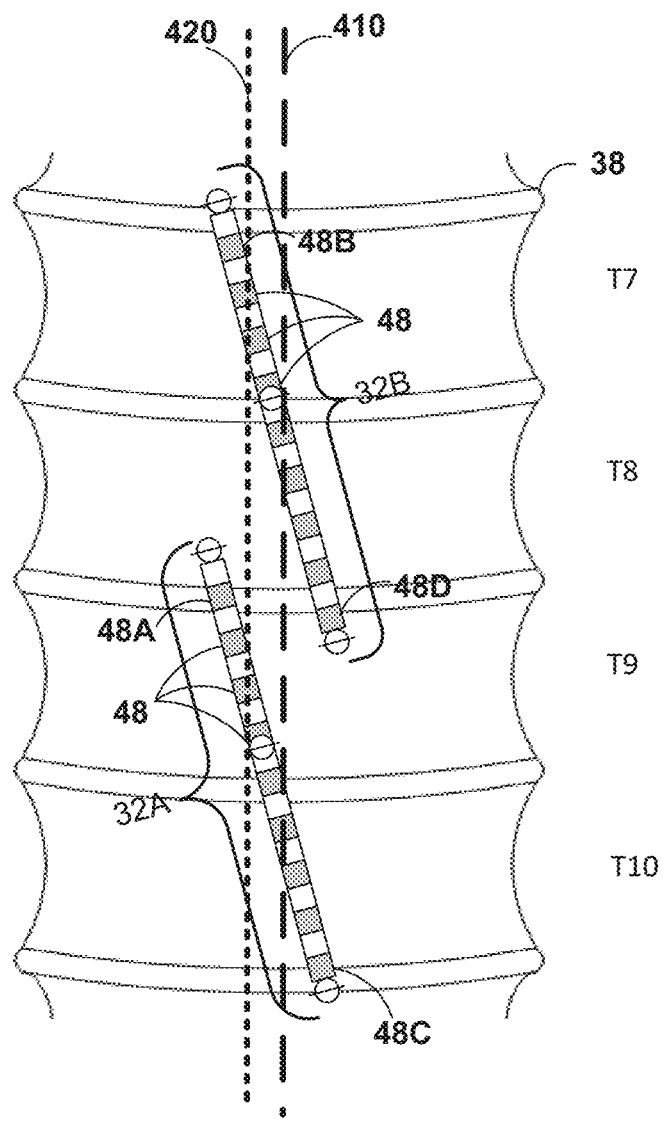
FIGS. 4A-4B are illustrations of example leads for delivering electrical neurostimulation in accordance with the techniques of the disclosure.
Figure 4B:
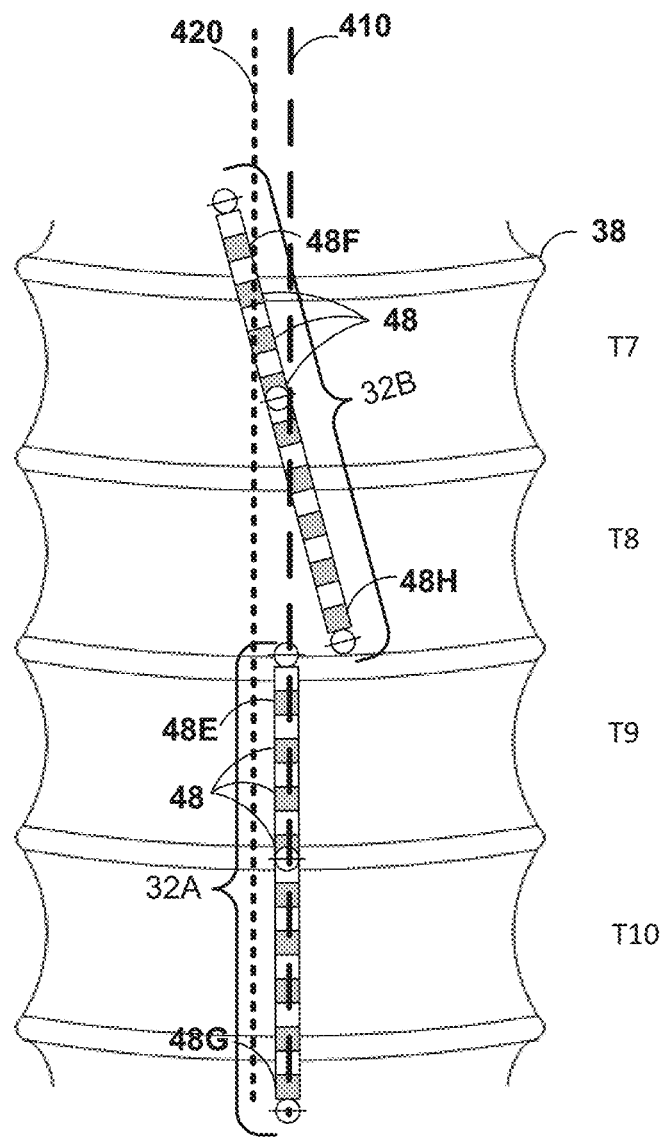

FIGS. 4A-4B are illustrations of example leads for delivering electrical neurostimulation in accordance with the techniques of the disclosure. The examples of FIGS. 4A-4B depict implantable medical leads 32 implanted along T6-T7 vertebrae of spine 38 of patient 36. Each of leads 32 further includes a plurality of electrodes 48.

In the example of FIG. 4A, a clinician implants leads 32A and 32B parallel to each other and at an angle relative to and across anatomical midline 410 of spinal cord 38 of patient 36. In some examples, the clinician implants leads 32A and 32B at an angle of 5-20 degrees relative to anatomical midline 410 of spinal cord 38 of patient 36. Such an implantation procedure as described herein may ensure that at least some of the electrodes are implanted on either side of physiological midline 420 of spinal cord 38. For example, an electrode combination including electrodes 48A of lead 32A and 48B of lead 32B are disposed on either side of physiological midline 420, and therefore may cause suppression of a pain sensation and/or paresthesia on both a left and a right lateral side of patient 36. However, an electrode combination including electrodes 48C of lead 32A and 48D of lead 32B does not include electrodes to the left lateral side of physiological midline 420. Thus, electrical stimulation via electrodes 48C and 48D may only cause suppression of a pain sensation and/or paresthesia on a right lateral side of patient 36. By testing various combinations of electrodes 48, the clinician may determine a combination of electrodes that lies to both a left and a right lateral side of patient 36, and thereby determine the electrode combination that provides the greatest pain relief to the patient.

In the example of FIG. 4B, a clinician implants lead 32A parallel to and offset from anatomical midline 410 of spinal cord 38 and implants lead 32B at an angle of 5-20 degrees relative to anatomical midline 410 of spinal cord 38 of patient 36. Such an implantation procedure as described herein may ensure that at least several electrodes are implanted on either side of the physiological midline of spinal cord 38.

For example, an electrode combination including electrodes 48G of lead 32A and 48F of lead 32B are disposed on either side of physiological midline 420, and therefore may cause suppression of a pain sensation and/or paresthesia on both a left and a right lateral side of patient 36. However, an electrode combination including electrodes 48E of lead 32A and 48H of lead 32B does not include electrodes to the left lateral side of physiological midline 420. Thus, electrical stimulation via electrodes 48E and 48H may only cause suppression of a pain sensation and/or paresthesia on a right lateral side of patient 36. By testing various combinations of electrodes 48, the clinician may determine a combination of electrodes that lies to both a left and a right lateral side of patient 36, and thereby determine the electrode combination that provides the greatest pain relief to the patient.

FIGS. 5A-5D illustrate an exemplary screen shot 500 of a display on user interface 59 of programmer 40, in accordance with the techniques of the disclosure. In one example, programmer 40 may be a clinician programmer. FIGS. 5A-5D are discussed in the context of a patient receiving spinal cord stimulation therapy as an illustrative example. A programmer, e.g., programmer 40, may receive user input via the user interface 59 to set up leads and parameters that define one or more stimulation programs for delivering therapy to a patient. A stimulation program may be delivered by an implantable stimulator individually or in combination with other programs, e.g., on a time-interleaved basis. A program may define an electrode combination, including a selected set of electrodes for delivery of stimulation and polarities of such electrodes, pulse current or pulse voltage amplitudes delivered by respective electrodes, pulse width and pulse rate. The user may set up a profile for the session and the patient, and proceed to configure placement of the leads.

Figure 5A:
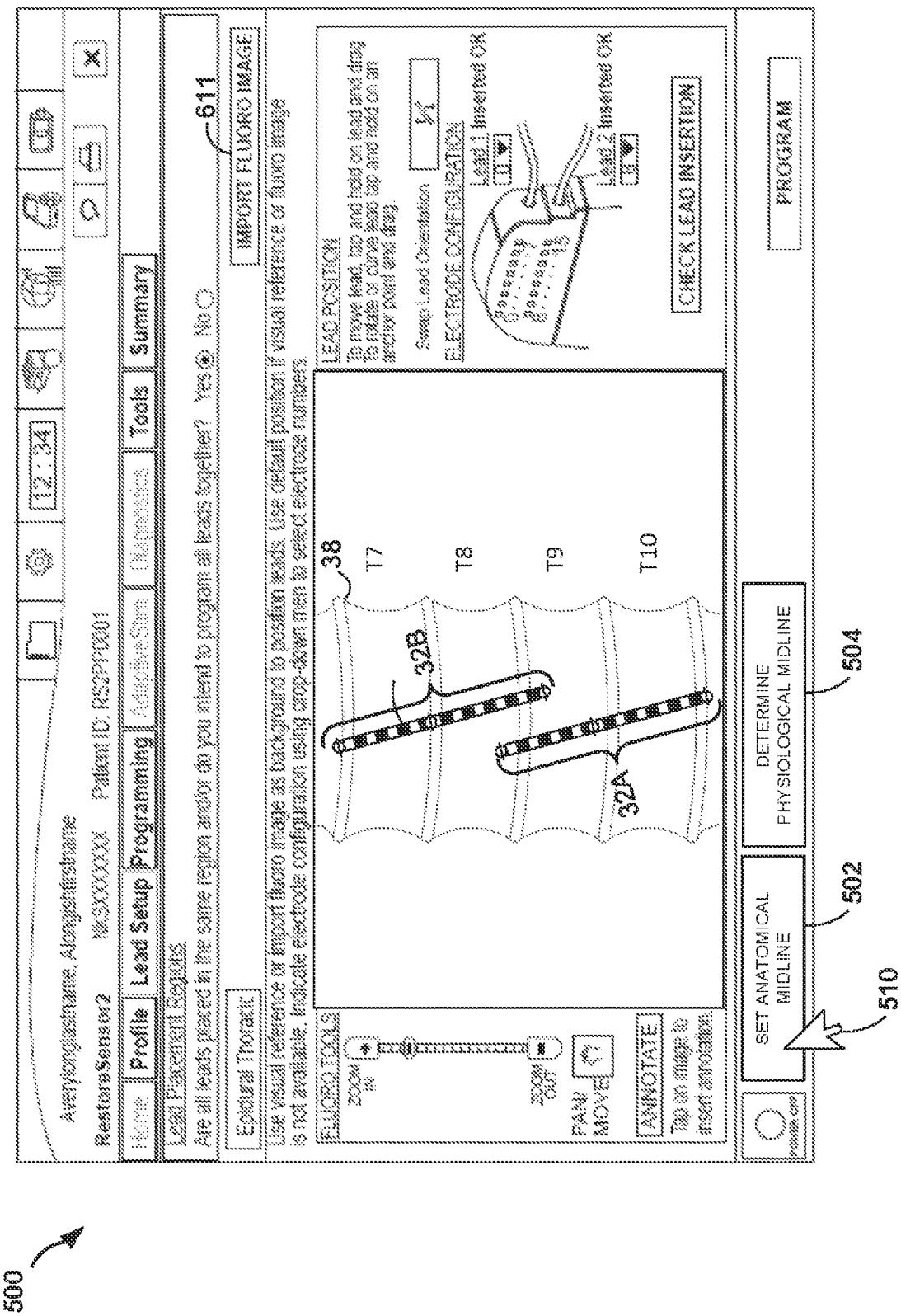
FIGS. 5A-5D illustrate an exemplary screen shot of a display on a user interface of an external programmer, in accordance with the techniques of the disclosure.

To provide an accurate representation of implanted leads for spinal cord stimulation, the user may select which leads will be programmed with therapy. In this example, there are up to 2 leads from which a user may select. However, in other examples there may be more or less leads available to the user from which to select. FIG. 5A illustrates a lead set up screen where the user is prompted to indicate whether all the leads, for the given number of leads implanted or being trialed, will be placed in the same region and/or programmed together by indicating "Yes" or "No." The user may assign implanted leads to one or more regions, where the regions represent the anatomical implant location of the leads associated with the regions. A lead region may be, for example, such entity as "lumbar spine" or "epidural thoracic." In one example, where different leads are selected for different regions, the user may view and/or program each region where only the leads associated with a selected region are viewed and/or programmed. In one example, the user may assign the case electrodes to one or more regions, either alone or in combination with the implanted leads.

Upon selecting the leads, a representation of the leads to be programmed for that region may be shown on the screen. Referring to FIG. 5A, the graphical representation of two leads 32, each with 8 electrodes may be shown on the screen, because the user selected to program them all together (in this example two leads). The user may be presented with an option to import an image for the lead region being programmed. The image may be for example a fluoroscopic image of the region in which therapy is to be applied. A button 611 labeled "Import Fluoro Image" appears on the display as shown in FIG. 5A, which the user may select if the user opts to import a fluoroscopic image of the leads assigned to the region for which therapy is being programmed. In another example, the display may also have a "Start Camera" button (not shown), which may, upon selection by the user, display an image acquired by the camera, which the user may select to use as the background image, as an alternative for importing a previously-acquired image. Therefore, a user may have an option to either use a camera or import a previously-acquired image. One or more examples of acquiring and storing a fluoroscopic image of a therapy region in a patient may be described in U.S. Pat. No. 8,744,591 to Davis et al., titled "STORING IMAGE OF THERAPY REGION IN IMPLANTABLE MEDICAL DEVICE," issued on Jun. 3, 2014 and in U.S. patent application Ser. No. 14/085,573 to Davis et al., titled "ASSIGNMENT AND MANIPULATION OF IMPLANTABLE LEADS IN DIFFERENT ANATOMICAL REGIONS WITH IMAGE BACKGROUND" and filed on Nov. 20, 2013, the entire content of each of which is incorporated herein by reference.

The display screen may also present options to the user to manipulate the positions or the representation of the leads 32. In the example of FIG. 5A, the user may move a lead 32 by tapping and holding on the lead 32 and dragging it, or the user may rotate or curve a lead 32 by tapping and holding on an anchor point and dragging as indicated by instructions provided to the user on the screen. The user may also swap the orientation of leads 32 by selecting the corresponding function button. The user may also manipulate the leads 32 further by bending, resizing, and shaping the graphical representation of the leads or portions of the leads to achieve a better match between the graphical leads and the image of the leads in the anatomical background image. In one example, the user may select starting and ending points of the leads 32 in the image (e.g., to match distal and proximal electrode locations in the image), and the programmer may automatically draw the graphical representation of the leads 32 between the two points. The display may also show the electrode configuration, showing how the leads 32 are inserted. In one example, an option may be displayed to "Check Lead Insertion" to check that the leads are inserted correctly. The display may also present the user with the ability to manipulate the fluoroscopic image, as shown on the left side of the screen. However, the fluoroscopic image tools may not be highlighted until a fluoroscopic image is imported.

In some examples, upon importing a fluoroscopic image of spinal cord 38, the representation of the leads 32 may be superimposed on the fluoroscopic image of spinal cord 38. While it is not shown, a similar screen may be displayed for each of the regions when multiple regions are defined, and the user may import a fluoroscopic image to one or more regions, by clicking on a tab for the region and clicking on the "Import Fluoro Image" for that region.

In one example, the user interface may display the image and graphical representation of leads in 2D. In this example, the user interface may display the same region and the corresponding graphical representation of leads implanted in the region in 2D from different perspectives corresponding to different angles or cross sections, as the implanted leads may curve in more than one direction spatially, and allow the user to manipulate the graphical representation of leads for each perspective. In another example, the user interface may display the image and graphical representation of leads in 3D. In this example, the user interface may display the region and the corresponding graphical representation of leads implanted in the region in 3D, and may allow the user to rotate and manipulate the image and the graphical representation in all directions.

After the leads and fluoroscopic image have been manipulated to match for a given region, the process may be repeated for all lead regions (if multiple regions are programmed). The fluoroscopic image may be compressed and stored in the device, by selecting the button labeled "Program" on the screen. Selecting "program" may program all the changes to the device. The display may also present the user with other options like "Tools" and "Summary" in addition to "Programming." Subsequently, the creation of therapy may occur (per lead region) on the final lead representation of the leads with the fluoroscopic image as background.

Each process described for the example of assigning all the leads to one image, may be used with each of the different regions. When multiple regions are defined, multiple fluoroscopic images may be linked to corresponding multiple lead electrode images and locations, and attributes related to the leads and the images may be linked thereto, and the combination of the images, leads, and attributes may be programmed and stored on medical devices, such as implantable stimulator 34 of FIG. 1. Each of the images may be associated with an anatomical region, or with different perspectives of the same region, for example. Additionally, a lead 32 may be programmed to provide therapy associated with more than one region. In one example, the user may assign and program the case electrodes for certain anatomical regions in the same manner the user assigns and programs implanted leads.

Figure 5B:
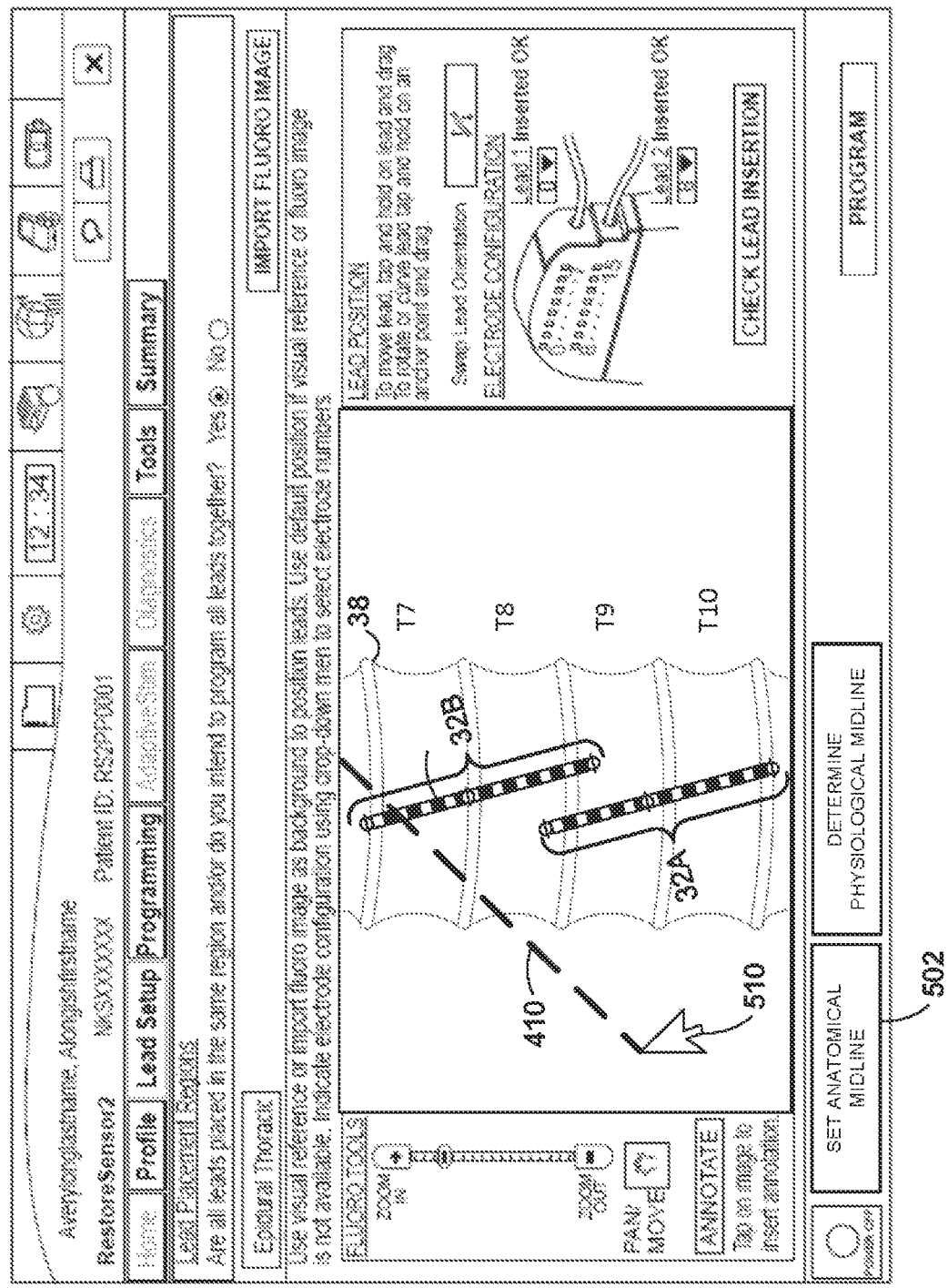

According to the techniques of the disclosure, the clinician may use user interface 500 to mark, in reference to the first and second leads 32, the location of the anatomical midline 410 of spinal cord 38 via a fluoroscope. As depicted in FIG. 5A, the clinician selects, via cursor 510, button 502 to set an anatomical midline of spinal cord 38 of patient 34. In the example of FIG. 5B, the clinician sets a position for the anatomical midline by using cursor 510 to drag a line 410 representing the anatomical midline of the spinal cord 38 over a fluoroscopic image of spinal cord 38. In some examples, upon setting a position of the anatomical midline of the spinal cord 38, the clinician may determine the location of the physiological midline of spinal cord 38 via patient feedback, and mark the location of the physiological midline of spinal cord 38 on user interface 500 in a similar fashion to that of the anatomical midline 410.

Figure 5C:
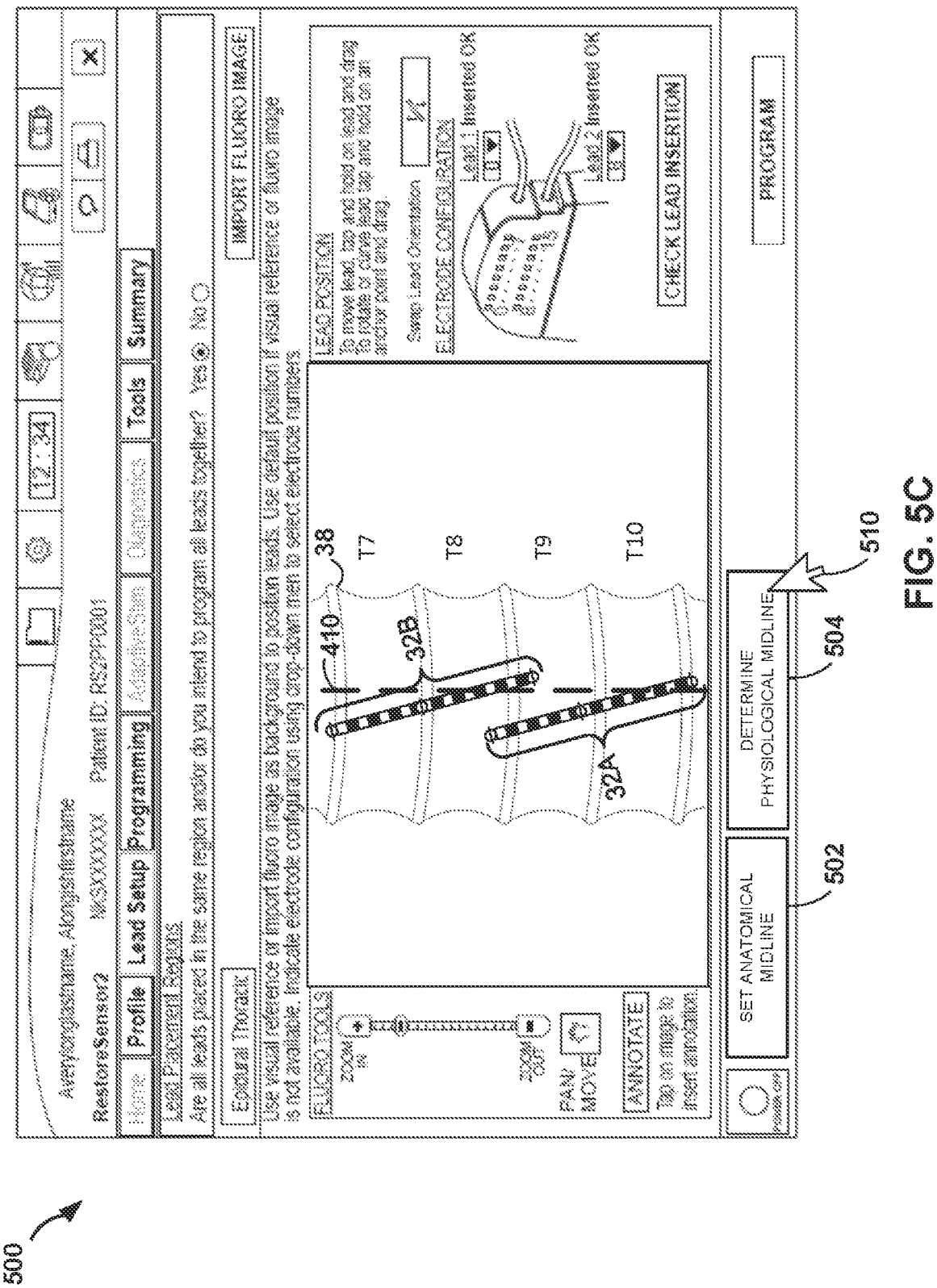
Figure 5D:
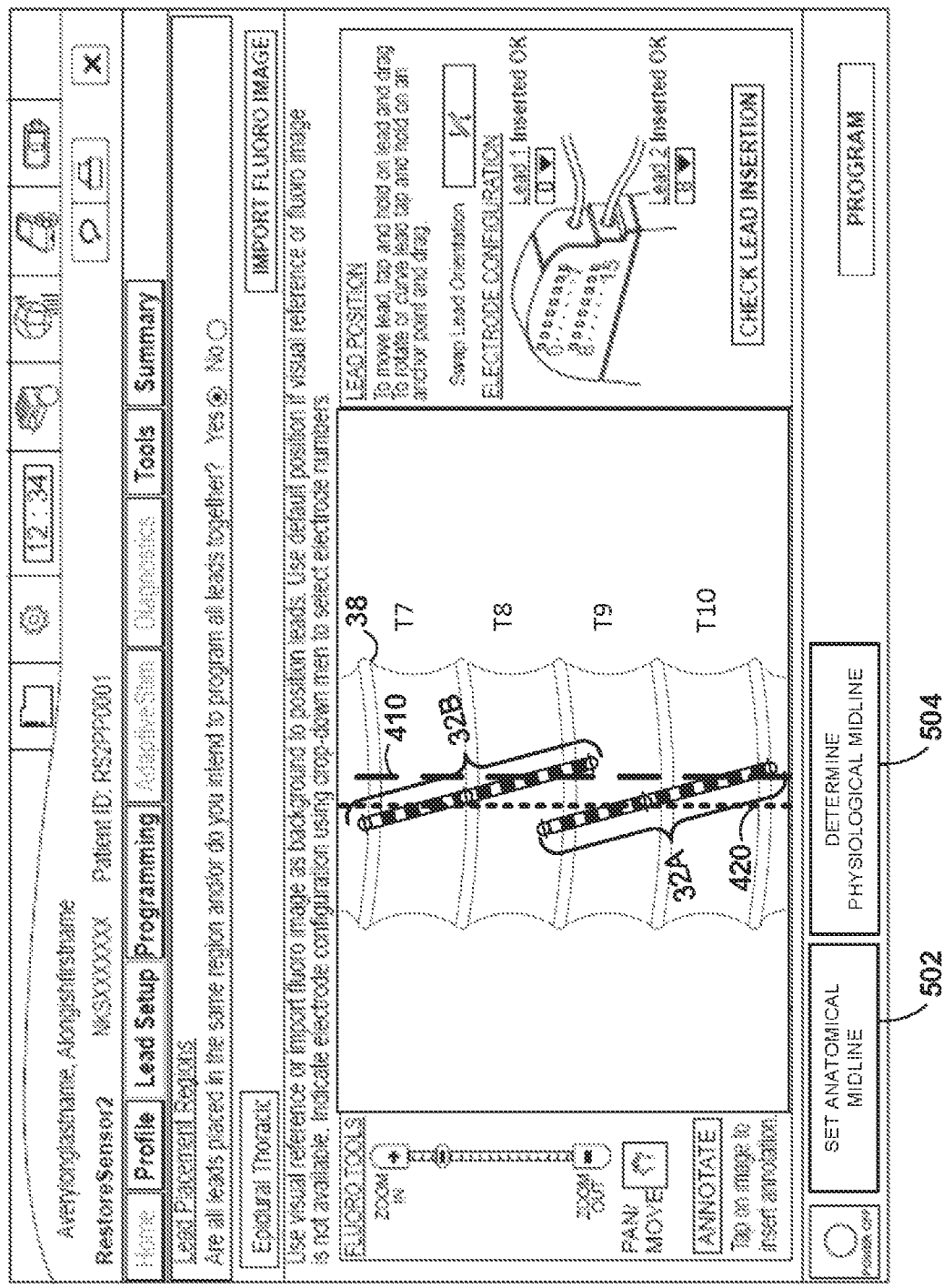

In further examples, as illustrated in FIG. 5C, user interface 500 includes a button 504 to determine the physiological midline of spinal cord 38. Upon setting a position of the anatomical midline of the spinal cord 38, the clinician may select button 504 via cursor 510. In response to the clinician selecting button 504, processor 53 of external programmer 40 determines a position of the physiological midline of spinal cord 38. As described above, processor 50 may monitor a physiological response of a tissue of patient 36 during delivery of electrical neurostimulation according to a plurality of different electrode combinations. In some examples, the tissue response is an evoked compound action potential (eCAP) response of a nerve fiber of patient 36. In some examples, the tissue response is a visible muscle twitching response of patient 36. For example, by determining that one or more electrode combinations evoke a response on only a right lateral side of patient 36, processor 50 may determine that the one or more electrode combinations are located to the right of the physiological midline of spinal cord 38. Further, by determining that one or more electrode combinations evoke a response on only a left lateral side of patient 36, processor 50 may determine that the one or more electrode combinations are located to the left of the physiological midline of spinal cord 38. By determining that one or more electrode combinations evoke a response on both a right and a left lateral side of patient 36, processor 50 may determine that at least some of the electrodes of the one or more electrode combinations are located both to the left and right of the physiological midline of spinal cord 38, e.g., the physiological midline of spinal cord 38 lies between the electrodes of the one or more electrode combinations. Accordingly, based on the physiological response of the tissue during delivery of electrical neurostimulation according to the plurality of different electrode combinations, processor 50 determines the position of the physiological midline 420. As depicted in FIG. 5D, processor 50 marks on user display 500 the position of physiological midline 420.

Figure 6:
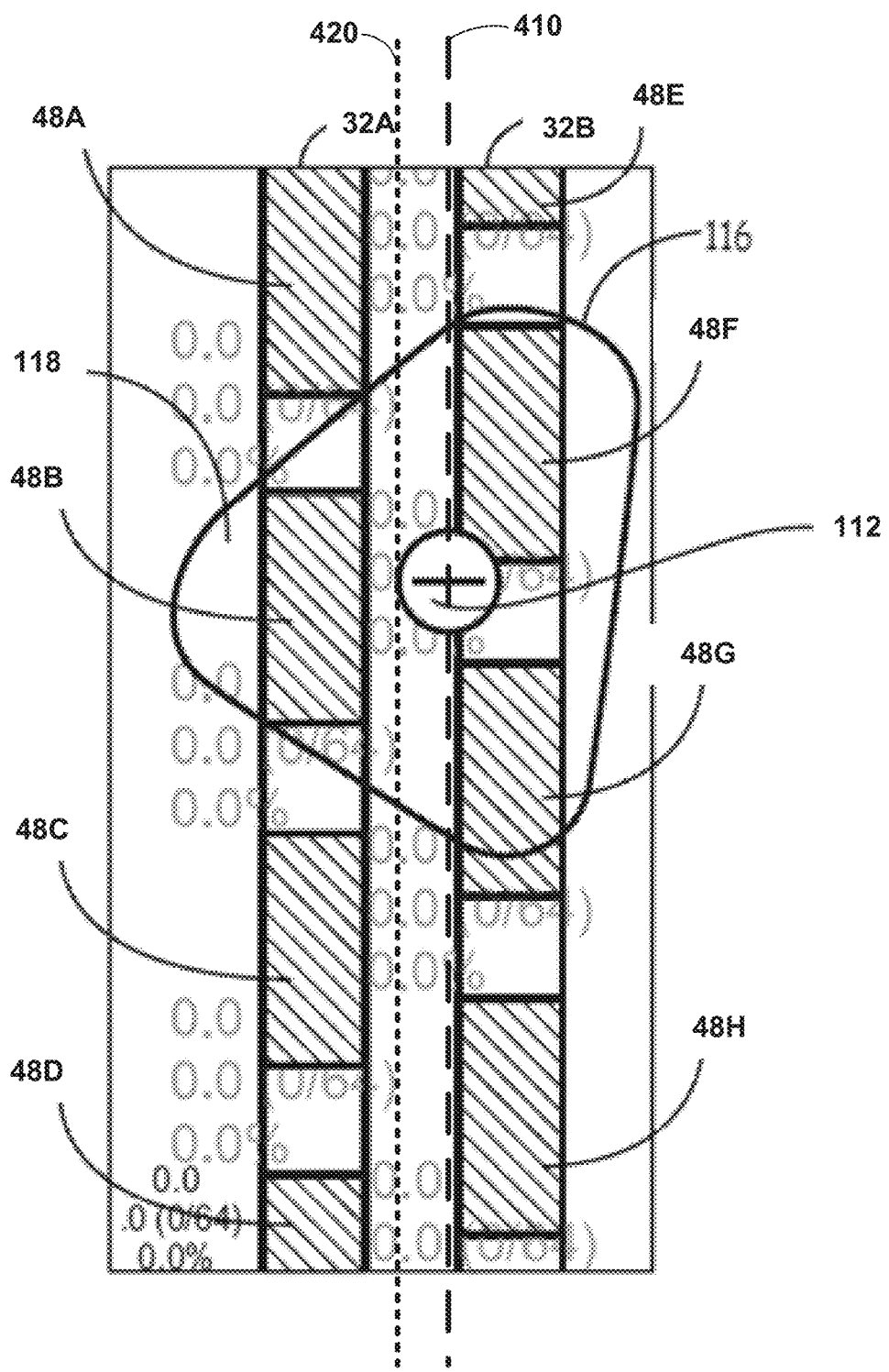
FIG. 6 is a conceptual diagram illustrating a stimulation zone of electrical stimulation therapy.

FIG. 6 is a conceptual diagram illustrating a stimulation zone of electrical stimulation therapy. As described above, system 30 delivers electrical neurostimulation according to a plurality of different combinations of electrodes 48. By monitoring a physiological response of a tissue of patient 36 during delivery of the electrical neurostimulation according to the plurality of different electrode combinations, system 30 may determine a position of a physiological midline 420 of spinal cord 38 of patient 36.

As depicted in FIG. 6, once the location of the physiological midline 420 of spinal cord 38, the clinician, via programmer 40, selects a combination of electrodes that includes one or more electrodes to a left lateral side of the determined physiological midline 420 and a right lateral side of physiological midline 420. For example, as depicted in FIG. 6, the clinician selects one or more electrodes that results in electrical field 116 that lies to a left lateral side of physiological midline 420 and a right lateral side of physiological midline 420. Implantable stimulator 34 uses electrodes 48B, 49F, and 48G to deliver electrical stimulation to a target tissue site 118 of patient 36. The centroid of electrical field 116 is indicated by icon 112.

In some examples, programmer 40 receives, from the clinician via user interface 59, a selection of one or more electrode combinations. In other examples, processor 53 of programmer 40 automatically determines a selection of one or more electrode combinations based on the detected location of physiological midline 420. In some examples, programmer 40 may automatically balance the anodes and cathodes of an electrode combination such that, after balancing, implantable stimulator 34 uses the same number of anodes and cathodes to deliver electrical stimulation to target tissue site 118. In other examples, programmer 40 selects an electrode combination that has differing numbers of anodes and cathodes. In yet other examples, programmer 40 selects an electrode combination that has a single anode and multiple cathodes. In yet other examples, programmer 40 selects an electrode combination that has multiple anodes and a single cathode. Additional techniques for selecting combinations of electrodes are provided in U.S. Pat. No.

8,560,080 to Goetz, issued on Oct. 15, 2013, the entire content of which is incorporated herein by reference.

Thus, by determining the location of the physiological midline 420, the system of the present disclosure may more accurately select an electrode combination for delivery of stimulation to patient 36. For example, by determining the location of the physiological midline, the system may select an electrode combination that includes one or more electrodes to a left lateral side of the determined physiological midline 420 and a right lateral side of physiological midline 420. By selecting such an electrode combination, the system of the present disclosure may create an electrical field 116 that stimulates tissue on both left lateral side and a right lateral side of patient 36. Alternatively, the system may select an electrode combination that includes one or more electrodes only to a left lateral side of the determined physiological midline 420 or only to a right lateral side of physiological midline 420. By selecting such an electrode combination, the system of the present disclosure may create an electrical field 116 that stimulates tissue on only a left lateral side or only a right lateral side of patient 36, respectively. Such a system may allow for increased reliability and efficacy in lead placement during surgery. Accordingly, a system as described herein may eliminate the need to perform testing of the implanted electrodes within the operation room, which may reduce the cost of the procedure, increase the reliability of the feedback received from the patient, and eliminate the need to wake the patient up from anesthesia to provide feedback on the electrical neurostimulation therapy, paresthesia, and pain sensations.

Figure 7:
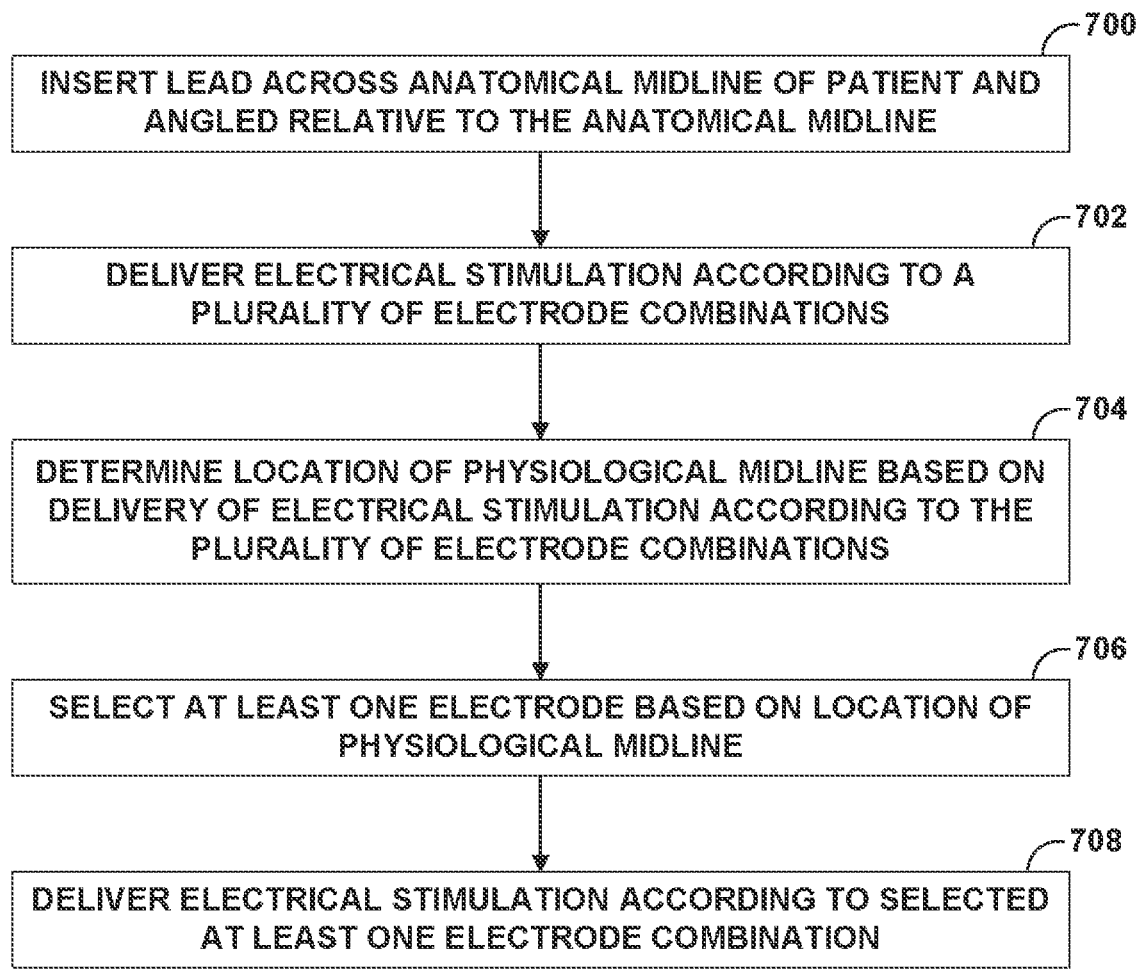
FIG. 7 is a flowchart depicting an example operation according to the techniques of the disclosure.

FIG. 7 is a flowchart depicting an example operation according to the techniques of the disclosure. For convenience, FIG. 7 is described with respect to FIG. 1. According to the techniques of the disclosure, a clinician implants at least one lead 32 at an angle relative to and across an anatomical midline of spinal cord 38 of patient 36 (700). In some examples, the at least one lead 32 is implanted at an angle of 5-20 degrees relative to the anatomical midline of spinal cord 38 of patient 36. In some examples of the techniques disclosed herein, the clinician implants a first lead 32A and second lead 32B angled 5-20 degrees relative to and across the anatomical midline of spinal cord 38. In alternate examples, the first lead 32A is implanted parallel to and offset from the physiological midline of spinal cord 38, while the second lead 32B is implanted at an angle of 5-20 degrees relative to and across the physiological midline of spinal cord 38. Such an implantation procedure as described herein may ensure that at least several electrodes are implanted on either side of the physiological midline of spinal cord 38.

After implanting the lead, the clinician, via external programmer 40, controls delivery of electrical stimulation according to a plurality of combinations of electrodes 48 (702). The clinician determines a location of a physiological midline of the patient 36 based on the delivery of electrical stimulation according to a plurality of combinations of electrodes 48 (704). In some examples, the clinician uses feedback from the patient regarding the different combinations of electrodes to identify a position of the physiological midline of spinal cord 38. In other examples, programmer 40 determines the location of a physiological midline based upon a tissue response of patient 36 to the electrical stimulation in the manner described above. The clinician may use a user interface to mark, in reference to the first and second leads, the location of the anatomical midline of spinal cord 38 via a fluoroscope, and to further mark the location of the physiological midline of spinal cord 38 via the patient feedback. Based on the location of the physiological midline of spinal cord 38, the clinician selects at least one electrode for subsequent delivery of electrical stimulation (706). Implantable stimulator 34 delivers electrical stimulation to patient 36 via the selected at least one electrode to provide pain relief therapy to patient 36 (708).

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:
1. A method comprising:
controlling, by one or more processors, an electrical neurostimulation therapy device to deliver electrical neurostimulation therapy to a patient via a plurality of combinations of a plurality of electrodes disposed on a first lead and a second lead connected to the electrical neurostimulation therapy device, wherein the first lead is positioned across an anatomical midline of a spinal cord of a patient and angled relative to the anatomical midline of the spinal cord so that at least one electrode of the plurality of electrodes disposed on the first lead is positioned to a left lateral side of the anatomical midline of the spinal cord and at least one other electrode of the plurality of electrodes disposed on the first lead is positioned to a right lateral side of the anatomical midline of the spinal cord, and wherein the second lead is positioned parallel to the spinal cord of the patient;

determining, by the one or more processors and for multiple combinations of the plurality of combinations of the plurality of electrodes, a therapeutic effect of the electrical neurostimulation therapy on the patient; and determining, by the one or more processors and based on the therapeutic effects on the patient of the multiple combinations of the plurality of combinations of the plurality of electrodes, a location of a physiological midline of the spinal cord of the patient relative to the multiple combinations of the plurality of combinations of the plurality of electrodes.

2. The method of claim 1, further comprising:
selecting, by the one or more processors and based on the location of the physiological midline relative to the multiple combinations of the plurality of combinations of the plurality of electrodes, one or more electrodes of the plurality of electrodes for delivery of subsequent electrical neurostimulation therapy to the patient; and
controlling, by the one or more processors, the electrical neurostimulation therapy device to deliver electrical neurostimulation therapy to the patient via the selected one or more electrodes of the plurality of electrodes.

3. The method of claim 2,
wherein selecting, based on the location of the physiological midline relative to the multiple combinations of the plurality of combinations of the plurality of electrodes, one or more electrodes of the plurality of electrodes for delivery of subsequent electrical neurostimulation therapy to the patient comprises:
selecting one or more first electrodes of the plurality of electrodes located to a left lateral side of the physiological midline; and
selecting one or more second electrodes of the plurality of electrodes located to a right lateral side of the physiological midline, and
wherein controlling the electrical neurostimulation therapy device to deliver electrical neurostimulation therapy to the patient via the selected one or more electrodes of the plurality of electrodes comprises controlling the electrical neurostimulation therapy device to deliver electrical neurostimulation therapy to the patient via the one or more first electrodes and the one or more second electrodes.

4. The method of claim 1, wherein determining the therapeutic effect of the electrical neurostimulation therapy on the patient comprises determining that the electrical neurostimulation therapy on the patient causes one of:
a paresthesia sensation in both a left lateral side and a right lateral side of the patient;
a paresthesia sensation in the left lateral side and not the right lateral side of the patient;
a paresthesia sensation in the right lateral side and not the right lateral side of the patient; or
no paresthesia sensation in either the left lateral side or the right lateral side of the patient.

5. The method of claim 1, wherein determining the therapeutic effect of the electrical neurostimulation therapy on the patient comprises determining that the electrical neurostimulation therapy on the patient causes one of:
a suppression of a pain sensation in both a left lateral side and a right lateral side of the patient;
a suppression of a pain sensation in the left lateral side and not the right lateral side of the patient;

a suppression of a pain sensation in the right lateral side and not the right lateral side of the patient; or
no suppression of a pain sensation in either the left lateral side or the right lateral side of the patient.

6. The method of claim 1, wherein determining the therapeutic effect of the electrical neurostimulation therapy on the patient comprises determining a response of a tissue of the patient to the electrical neurostimulation therapy.

7. The method of claim 1,
wherein determining, for the multiple combinations of the plurality of combinations of the plurality of electrodes, the therapeutic effect of the electrical neurostimulation therapy comprises:
determining that electrical neurostimulation therapy delivered with a first combination of the plurality of combinations of the plurality of electrodes causes a first therapeutic effect in the left lateral side and not the right lateral side of the patient; and
determining that electrical neurostimulation therapy delivered with a second combination of the plurality of combinations of the plurality of electrodes causes a second therapeutic effect in the right lateral side and not the left lateral side of the patient, and
wherein determining, based on the therapeutic effects on the patient of the multiple combinations of the plurality of combinations of the plurality of electrodes, the location of the physiological midline of the spinal cord of the patient relative to the multiple combinations of the plurality of combinations of the plurality of electrodes comprises determining, based on the first and second therapeutic effects, that the physiological midline of the spinal cord of the patient is located between the first combination of the plurality of combinations of the plurality of electrodes and the second combination of the plurality of combinations of the plurality of electrodes.

8. The method of claim 1,
wherein the second lead is positioned substantially inferior to the first lead so that the first lead and second lead at least partially do not overlap along a longitudinal axis of the patient.

9. A system comprising:
a first lead positioned across an anatomical midline of a spinal cord of a patient and angled relative to the anatomical midline of the spinal cord so that at least one electrode of a first plurality of electrodes disposed on the first lead is positioned to a left lateral side of the anatomical midline of the spinal cord and at least one other electrode of the first plurality of electrodes is positioned to a right lateral side of the anatomical midline of the spinal cord, wherein the first lead is connected to an electrical neurostimulation therapy device;
a second lead positioned parallel to the spinal cord of the patient, the second lead having a second plurality of electrodes, and wherein the second lead is connected to the electrical neurostimulation therapy device;
the electrical neurostimulation therapy device, wherein the electrical neurostimulation therapy device is configured to deliver electrical neurostimulation therapy to the patient via a plurality of combinations of the first plurality of electrodes and the second plurality of electrodes; and
one or more processors configured to:
control the electrical neurostimulation therapy device to deliver electrical neurostimulation therapy to the patient via the plurality of combinations of the first plurality of electrodes and the second plurality of electrodes:
  determine, for multiple combinations of the plurality of combinations of the first plurality of electrodes and the second plurality of electrodes, a therapeutic effect of the electrical neurostimulation therapy on the patient; and
  determine, based on the therapeutic effects on the patient of the multiple combinations of the plurality of combinations of the first plurality of electrodes and the second plurality of electrodes, a location of a physiological midline of the spinal cord of the patient relative to the multiple combinations of the plurality of combinations of the first plurality of electrodes and the second plurality of electrodes.

10. The system of claim 9, wherein the one or more processors are further configured to:
  select, based on the location of the physiological midline relative to the multiple combinations of the plurality of combinations of the first plurality of electrodes and the second plurality of electrodes, one or more electrodes of the first plurality of electrodes and the second plurality of electrodes for delivery of subsequent electrical neurostimulation therapy to the patient; and
  control the electrical neurostimulation therapy device to deliver electrical neurostimulation therapy to the patient via the selected one or more electrodes of the first plurality of electrodes and the second plurality of electrodes.

11. The system of claim 10,
  wherein to select, based on the location of the physiological midline relative to the multiple combinations of the plurality of combinations of the first plurality of electrodes and the second plurality of electrodes, one or more electrodes of the first plurality of electrodes and the second plurality of electrodes for delivery of subsequent electrical neurostimulation therapy to the patient, the one or more processors are further configured to:
    select one or more first electrodes of the first plurality of electrodes and the second plurality of electrodes located to a left lateral side of the physiological midline; and
    select one or more second electrodes of the first plurality of electrodes and the second plurality of electrodes located to a right lateral side of the physiological midline, and
  wherein to control the electrical neurostimulation therapy device to deliver electrical neurostimulation therapy to the patient via the selected one or more electrodes of the fist plurality of electrodes and the second plurality of electrodes, the one or more processors are further configured to control the electrical neurostimulation therapy device to deliver electrical neurostimulation therapy to the patient via the one or more first electrodes and the one or more second electrodes.

12. The system of claim 9, wherein to determine the therapeutic effect of the electrical neurostimulation therapy on the patient, the one or more processors are configured to determine that the electrical neurostimulation therapy on the patient causes one of:
  a paresthesia sensation in both a left lateral side and a right lateral side of the patient;
  a paresthesia sensation in the left lateral side and not the right lateral side of the patient;
  a paresthesia sensation in the right lateral side and not the right lateral side of the patient; or
  no paresthesia sensation in either the left lateral side or the right lateral side of the patient.

13. The system of claim 9, wherein to determine the therapeutic effect of the electrical neurostimulation therapy on the patient, the one or more processors are configured to determine that the electrical neurostimulation therapy on the patient causes one of:
  a suppression of a pain sensation in both a left lateral side and a right lateral side of the patient;
  a suppression of a pain sensation in the left lateral side and not the right lateral side of the patient;
  a suppression of a pain sensation in the right lateral side and not the right lateral side of the patient; or
  no suppression of a pain sensation in either the left lateral side or the right lateral side of the patient.

14. The system of claim 9, wherein to determine the therapeutic effect of the electrical neurostimulation therapy on the patient, the one or more processors are configured to determine a response of a tissue of the patient to the electrical neurostimulation therapy.

15. The system of claim 9,
  wherein to determine, for the multiple combinations of the plurality of combinations of the first plurality of electrodes and the second plurality of electrodes, the therapeutic effect of the electrical neurostimulation therapy, the one or more processors are configured to:
    determine that electrical neurostimulation therapy delivered with a first combination of the plurality of combinations of the first plurality of electrodes and the second plurality of electrodes causes a first therapeutic effect in the left lateral side and not the right lateral side of the patient; and
    determine that electrical neurostimulation therapy delivered with a second combination of the plurality of combinations of the s plurality of electrodes and the second plurality of electrodes causes a second therapeutic effect in the right lateral side and not the left lateral side of the patient, and
  wherein to determine, based on the therapeutic effects on the patient of the multiple combinations of the plurality of combinations of the first plurality of electrodes and the second plurality of electrodes, the location of the physiological midline of the spinal cord of the patient relative to the multiple combinations of the plurality of combinations of the first plurality of electrodes and the second plurality of electrodes, the one or more processors are configured to determine, based on the first and second therapeutic effects, that the physiological midline of the spinal cord of the patient is located between the first combination of the plurality of combinations of the first plurality of electrodes and the second plurality of electrodes and the second combination of the plurality of combinations of the first plurality of electrodes and the second plurality of electrodes.

16. A method comprising
  delivering, with an electrical neurostimulation therapy device, electrical neurostimulation therapy to the patient via a plurality of combinations of a first plurality of electrodes disposed on a first lead connected to the electrical neurostimulation therapy device and a second plurality of electrodes disposed along a second lead connected to the electrical neurostimulation therapy device,
  wherein the first lead is positioned across an anatomical midline of a spinal cord of a patient and angled relative to the anatomical midline of the spinal cord so that at least one electrode of the first plurality of electrodes disposed on the first lead is positioned to a left lateral side of the anatomical midline of the spinal cord and at least one other electrode of the first plurality of electrodes is positioned to a right lateral side of the anatomical midline of the spinal cord, and wherein the second lead is positioned parallel to the anatomical midline of the spinal cord of the patient and wherein the second lead is positioned substantially inferior to the first lead so that the first lead and second lead at least partially do not overlap along a longitudinal axis of the patient.

\* \* \* \* \*